(12) United States Patent
Gibbins et al.

(10) Patent No.: US 6,897,349 B2
(45) Date of Patent: May 24, 2005

(54) SILVER-CONTAINING COMPOSITIONS, DEVICES AND METHODS FOR MAKING

(75) Inventors: Bruce L. Gibbins, Lake Oswego, OR (US); Lance D. Hopman, Tigard, OR (US)

(73) Assignee: Acrymed, Portland, OR (US)

( * ) Notice: Subject to any disclaimer, the term of this patent is extended or adjusted under 35 U.S.C. 154(b) by 112 days.

(21) Appl. No.: 10/441,275

(22) Filed: May 19, 2003

(65) Prior Publication Data

US 2004/0010215 A1 Jan. 15, 2004

Related U.S. Application Data

(63) Continuation of application No. 09/675,892, filed on Sep. 29, 2000, now Pat. No. 6,605,751, and a continuation-in-part of application No. 09/191,223, filed on Nov. 13, 1998, now Pat. No. 6,355,858, which is a continuation-in-part of application No. 08/971,074, filed on Nov. 14, 1997, now Pat. No. 5,928,174.
(60) Provisional application No. 60/212,455, filed on Jun. 19, 2000, and provisional application No. 60/157,000, filed on Oct. 1, 1999.

(51) Int. Cl.[7] .................... A61F 13/00; A61M 35/00; B05D 1/18
(52) U.S. Cl. ...................... 602/48; 602/43; 427/2.1; 424/423; 424/445; 424/617; 424/619; 424/630; 604/289; 604/304
(58) Field of Search ............ 602/41–59; 442/443–449; 604/289, 304, 305–308; 427/2.1, 2.25

(56) References Cited

U.S. PATENT DOCUMENTS

| | | |
|---|---|---|
| 2,934,066 A | 4/1960 | Stowasser |
| 3,092,552 A | 6/1963 | Romans |
| 3,157,524 A | 11/1964 | Artandi |
| 3,645,835 A | 2/1972 | Hodgson |
| 3,969,498 A | 7/1976 | Catania et al. |
| 4,306,551 A | 12/1981 | Hymes et al. |
| 4,320,201 A | 3/1982 | Berg et al. |
| 4,340,043 A | 7/1982 | Seymour |
| 4,483,688 A | 11/1984 | Akiyama |
| 4,529,623 A | 7/1985 | Maggs |
| 4,612,337 A | 9/1986 | Fox, Jr. et al. |
| 4,686,211 A | 8/1987 | Hara et al. |

(Continued)

FOREIGN PATENT DOCUMENTS

| | | |
|---|---|---|
| EP | 0 072 251 A | 2/1983 |
| EP | 0 489 206 A | 6/1992 |
| EP | 0 707 793 A | 4/1996 |
| GB | 1471013 | 4/1977 |
| GB | 1 554 002 A | 10/1979 |
| GB | 2134791 A | 8/1984 |
| WO | WO 84/01721 | 5/1984 |
| WO | WO 99 25395 A | 5/1999 |
| WO | WO 01/24839 A1 | 4/2001 |

OTHER PUBLICATIONS

*Progress in Medicinal Chemistry*, A.D. Russel and W.B. Hugo, "Antimicrobial Activity and Action of Silver," vol. 31, G.P Ellis & D.K. Luscombe, ed., Elsevier Science B.V., pp. 351–370, (1994).

Grier, N., Ph.D., "Silver and Its Compounds," Disinfection, Sterilization, and Preservation, 3rd Edition, Seymour S. Block, ed. Lea & Febiger, Philadelphia, 1983, Chapter 18, pp. 375–389.

*Primary Examiner*—Kim M. Lewis
(74) *Attorney, Agent, or Firm*—Troutman Sanders LLP

(57) ABSTRACT

The present invention comprises methods and compositions for making a silver-containing antimicrobial hydrophilic material. More particularly, the present invention comprises methods and compositions for stabilized silver antimicrobial devices comprising a matrix comprising a polymer network and a non-gellable polysaccharide, and an active agent. The matrix may be formed into any desired shape for its desired uses.

105 Claims, 8 Drawing Sheets

U.S. PATENT DOCUMENTS

| | | |
|---|---|---|
| 4,902,503 A | 2/1990 | Umemura et al. |
| 5,023,082 A | 6/1991 | Friedman et al. |
| 5,100,668 A | 3/1992 | Edelman et al. |
| 5,196,190 A | 3/1993 | Nangia et al. |
| 5,326,567 A | 7/1994 | Capelli |
| 5,429,591 A | 7/1995 | Yamamoto et al. |
| 5,432,077 A | 7/1995 | Farrah |
| 5,470,585 A | 11/1995 | Gilchrist |
| 5,527,534 A | 6/1996 | Myhling |
| 5,567,495 A | 10/1996 | Modak et al. |
| 5,681,579 A | 10/1997 | Freeman |
| 5,709,870 A | 1/1998 | Yoshimura et al. |
| 5,725,491 A | 3/1998 | Tipton et al. |
| 5,744,151 A | 4/1998 | Capelli |
| 5,753,251 A | 5/1998 | Burrell et al. |
| 5,820,918 A | 10/1998 | Ronan et al. |
| 5,830,496 A | 11/1998 | Freeman |
| 5,863,548 A | 1/1999 | Elder |
| 6,471,982 B1 | 10/2002 | Lydon et al. |
| 6,669,981 B2 | 12/2003 | Parsons et al. |
| 2002/0073891 A1 | 6/2002 | Parsons et al. |

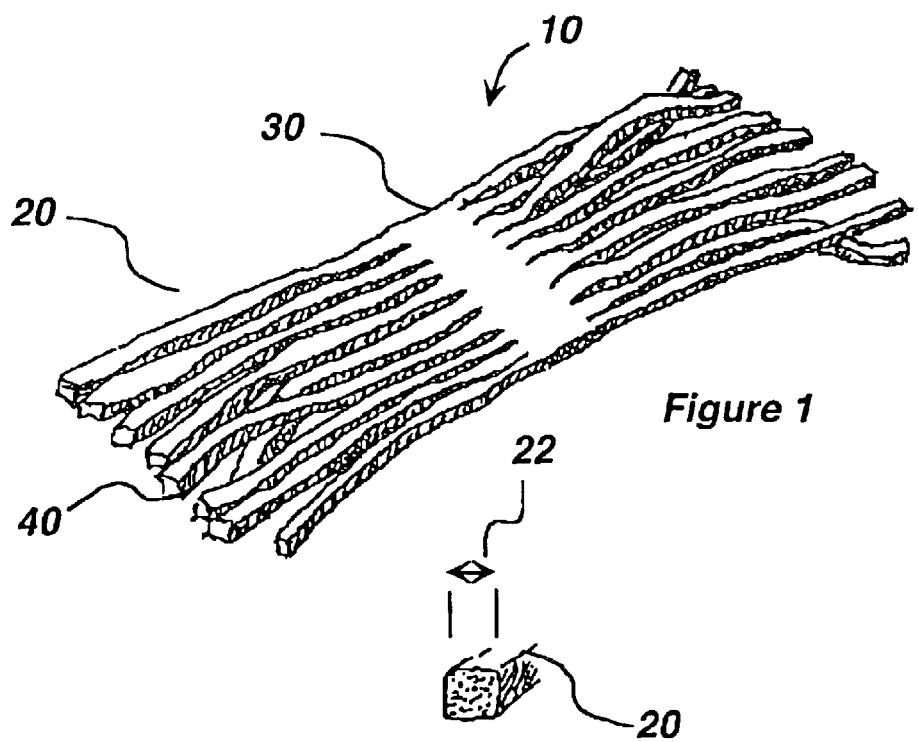
Figure 1
Figure 2
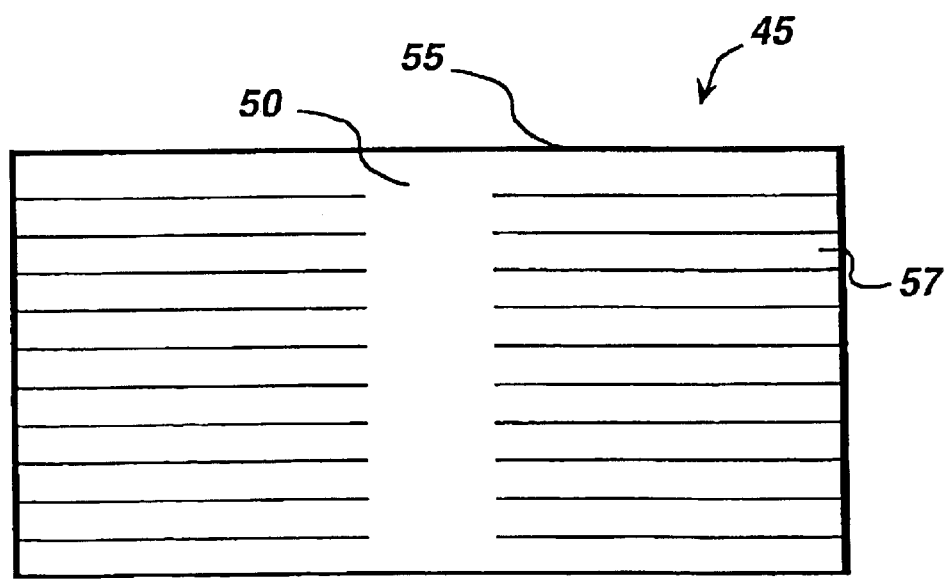
Figure 3

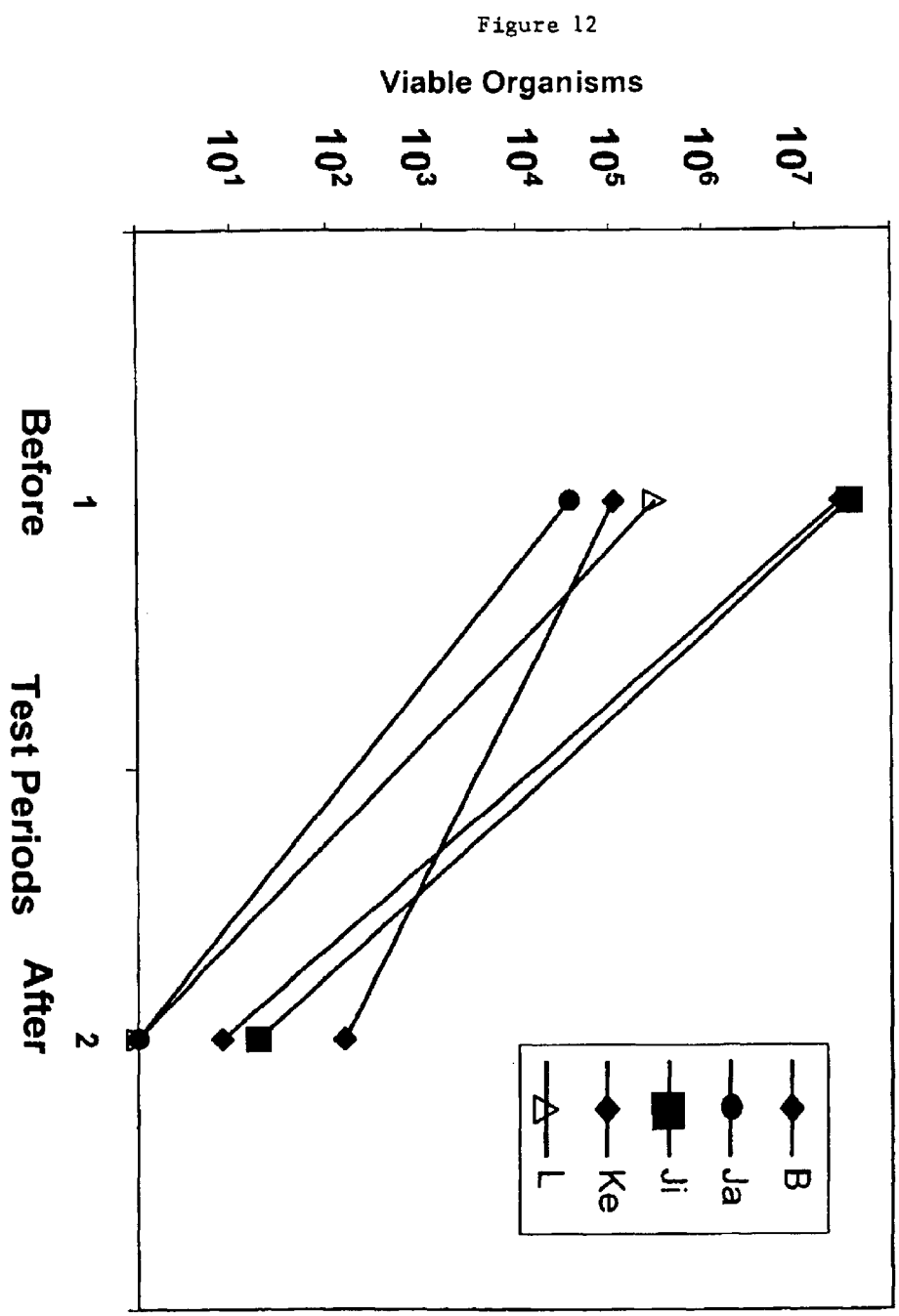

SILVER-CONTAINING COMPOSITIONS, DEVICES AND METHODS FOR MAKING

CROSS REFERENCE TO RELATED APPLICATIONS

This application is a continuation of application Ser. No. 09/675,892, filed Sep. 29, 2000, now U.S. Pat. No. 6,605,757, which claims the priority of U.S. Provisional Patent Application No. 60/157,000, filed Oct. 1, 1999, U.S. Provisional Patent Application No. 60/212,455, filed Jun. 19, 2000, and is a continuation-in-part of U.S. patent application Ser. No. 09/191,223 filed Nov. 13, 1998 now U.S. Pat. No. 6,355,858 which is a continuation-in-part of application Ser. No. 08/971,074, filed on Nov. 14, 1997, now U.S. Pat. No. 5,928,174.

FIELD OF THE INVENTION

The present invention relates generally to antimicrobial devices and methods for making and using such devices and particularly to compositions and methods for delivering active agents to wounds. More particularly, the present invention relates to methods of making antimicrobial matrices for uses in many areas, including treatment of wounds.

BACKGROUND OF THE INVENTION

The outer layer of skin surrounding the body performs an important protective function as a barrier against infection, and serves as a means of regulating the exchange of heat, fluid and gas between the body and external environment. When skin is removed or damaged by being abraded, burned or lacerated, this protective function is diminished. Areas of damaged skin are conventionally protected by the application of a wound dressing which facilitates wound healing by acting as a skin substitute.

Wounds to skin and the underlying tissues of humans and animals may be caused by external insult such as friction, abrasion, laceration, burning or chemical irritation. Damage to such tissues may also result from internal metabolic or physical dysfunction, including but not limited to bone protrudence, diabetes, circulatory insufficiencies, or inflammatory processes. Normally tissue damage initiates physiological processes of regeneration and repair. In broad terms, this process is referred to as the wound healing process.

The wound healing process usually progresses through distinct stages leading to the eventual closure, and restoration of the natural function of the tissues. Injury to the skin initiates an immediate vascular response characterized by a transient period of is vasoconstriction, followed by a more prolonged period of vasodilation. Blood components infiltrate the wound site, endothelial cells are released, exposing fibrillar collagen, and platelets attach to exposed sites. As platelets become activated, components are released which initiate events of the intrinsic coagulation pathway. At the same time, a complex series of events trigger the inflammatory pathways generating soluble mediators to direct subsequent stages of the healing process.

Normally, the wound healing process is uneventful and may occur regardless of any intervention, even in the case of acute or traumatic wounds. However, where an underlying metabolic condition or perpetual insult such as pressure or infection are contributing factors, the natural wound healing process may be retarded or completely arrested, resulting in a chronic wound. Trends in modern medical practices have shown that the wound healing of both acute and chronic wounds may be significantly improved by clinical intervention using methods and materials that optimize wound conditions to support the physiological processes of the progressive stages of wound healing. Key factors in providing the optimal conditions are the prevention of scab formation, prevention or control of microbial activity, and the maintenance of an optimal level of moisture in the wound bed. It is also helpful to manage wound exudate fluid.

A common problem in the management of both acute and chronic wounds is the maintenance of an optimal level of moisture over the wound bed during heavy exudate drainage. This is usually, but not always, an early stage of healing. Most moist wound dressing technologies such as thin films, hydrocolloid dressings and hydrogels are typically overwhelmed by the accumulated exudate moisture during this heavy drainage phase. Management of moisture during heavy exudate drainage often necessitates the use of gauze or sponge packings that wick away excess moisture from the wound bed, thin film coverings that trap exudate fluid over the wound bed, or calcium alginate dressings that chemically bind exudate moisture due to the hydroscopic properties of the seaweed extract.

Examples of wound dressings that have been developed include collagen dressings, a natural polymer. Soluble collagen has been used as a subcutaneous implant for repairing dermatological defects such as acne scars, glabellar furrows, excision scars and other soft tissue defects. Collagen has also been used in many forms as wound dressings such as collagen sponges. Several inventions have attempted to solve the problem of maintenance of an optimal level of moisture in the wound environment. Collagen is used as the matrix material in Artandi, U.S. Pat. No. 3,157,524 and Berg et al., U.S. Pat. No. 4,320,201. However, most of these dressings are not satisfactory for the various types of full thickness wounds. Collagen films and sponges do not readily conform to varied wound shapes. Furthermore, some collagen wound dressings have poor fluid absorption properties and undesirably enhance the pooling of wound fluids. Generally, most wound dressing materials do not provide for the control or elimination of microbial bioburden in the wounds.

Another example of wound dressings that have been developed for control of moisture levels in wounds are the hydrocolloid dressings. United Kingdom Patent Number 1,471,013 and Catania et al., U.S. Pat. No. 3,969,498 describe hydrocolloid dressings that are plasma soluble, form an artificial eschar with the moist elements at the wound site, and gradually dissolve to release medicaments. These dressings comprise a hydrophilic foam of dextran polymer that can be applied without therapeutic agents or ointments, are non-irritating to the lesion and can be easily removed.

Known hydrocolloid dressings in general, and the Catania et al. dressings in particular, are subject to a number of drawbacks. The major disadvantages of these dressings include the potential to disintegrate in the presence of excess fluid at the wound site, and minimal, virtually negligible, control over water loss from the wound. This latter disadvantage is particularly important, as excess water loss from a wound will cause an increase in heat loss from the body as a whole, potentially leading to hypermetabolism. In addition, hydrocolloid dressings require frequent dressing changes. This is especially true of the Catania et al. dressing due to the dissolution of the dextran polymer at the wound site caused by the fluid loss through the wound in the exudative stage.

Although currently available dressing materials possess features that contribute to the control of heavy exudate drainage, most also possess significant limitations that retard the overall healing process. For example, thin film dressings such as those described in U.S. Pat. No. 3,645,835, maintain excessive moisture over the wound bed, contributing to the overhydration or maceration of surrounding skin. Although sponges and gauze support tissue, they require frequent changing, and cause irritation to the wound bed during body movement and dressing removal. These dressings may be permeable to moisture but not to microorganisms. Although these devices and others administer some control over wound exudate moisture and may additionally provide a barrier to microbial contamination, they do not actively participate in controlling the growth of microorganisms or in the elimination of microbial bioburden from the wound dressing. Calcium alginates turn into a gelatinous mass during interaction with moisture, are difficult to remove completely, and often dehydrate the wound bed due to the hydroscopic nature of the matrix.

Importantly, none of the presently available devices significantly contribute to or support the autolytic debridement phase, which is the natural removal process of necrotic tissue and debris from the wound. Autolytic debridement is a key early stage event that precedes repair phases of healing. When wound conditions are not optimal for supporting autolytic debridement, then clinical procedures such as surgical removal, irrigation, scrubbing, and enzymatic or chemical methods must be used to remove the necrotic tissue and escar that can inhibit wound healing.

Temporary or permanent wound dressings that are designed to enhance wound healing are needed to cover large open wounds on patients with extensive burns, lacerations and skin damage. Furthermore the ability to produce wound dressings in a variety of shapes to accommodate multiple sizes and forms of injuries is important in the manufacture of useful medical products.

In addition, there continues to be a need for a wound dressing that possesses high moisture absorption capacity, a high rate of absorption, as well as a capacity to regulate moisture at the wound bed-dressing interface. Desirably, such a wound dressing device should stimulate the autolytic debridement process, especially during the heavy exudating phase of wound care management.

Another desirable aspect of a wound dressing would be the ability to deliver active agents to the site of injury to accelerate wound healing and in particular to control the growth and damage caused by microbial contaminants of the wound. Active agents for use in wound treatment may be administered to an individual in a variety of ways. For example, active agents may be administered topically, subingually, orally, or by injection (subcutaneous, intramuscular or intravenous). Nevertheless, there are drawbacks to many of these methods, and an inexpensive, reliable, localized and relatively pain-free method of administering an active agent has not been provided in the prior art.

One common method employed for the treatment of wounds is the topical application of a salve or ointment. Yet many times, topical application to a wound can be painful and short-lived. Additionally, in the case of a deeply cavitated wound in particular, an excess of active agent may be required because the agent must diffuse through layers of necrotic tissue and newly forming epidermal tissues. This difficulty in delivering the agent may require the application of an excessive amount of the agent and preclude an accurate determination of the effective amount of active agent to be added.

The oral and sublingual administrations of active agents used in wound treatment also have their drawbacks. Most importantly, the administration site, the mouth, is normally far removed from the actual location of the wound. Ingestion of an active agent at a site distant from the wound may result in the agent having negative system-wide effects and possibly knocking out the normal flora, or normal microbial environment, whose presence benefits an individual. Successful absorption of the agent into the bloodstream also depends on several factors such as the agent's stability in gastrointestinal fluids, the pH of the gastrointestinal tract, solubility of solid agents, intestinal motility, and gastric emptying.

Injection of an active agent, a normally painful method of administration, may have the same negative system-wide effects as that of an oral or sublingual administration if injection is at a site distant from the wound. Yet more importantly, a danger inherent in the injection of an active agent is that rapid removal of the agent is impossible once it is administered. There is also a risk of transmission of infections and the possibility of vascular injury due to the use of needles.

One active agent, silver, has long been recognized for its broad spectrum anti-microbial activity and compatibility with mammalian tissues. Although silver has been used in a large range of medical devices, its incorporation, as a prophylactic anti-infective agent, in primary wound contact products has been restricted due to silver's adverse properties. These properties include a short half-life, the rapid inactivation of silver by protein, and light-mediated discoloration of the product containing silver and any body parts touching the product, such as skin. Recently, manufacturers have tried methods to overcome some of the limitations to broaden the utility of silver in wound care. The currently available silver-containing wound care dressing materials have been unsuccessful in adequately overcoming the problems inherent in using silver.

Medical devices that are implanted or those that are attached to epithelia may create an environment conducive to the multiplication and growth of microorganisms. This microbial growth may lead to complications such as local or systemic infection. Dermal wounds are at particular risk since microbial contaminants are commonly present, and the wound produces optimal nutrients and other environmental conditions for microbial growth. Medical practices have demanded the use of sterile or low bioburden devices and the adoption of procedures and adjuncts such as frequent dressing changes, use of topical antimicrobial compounds, and systemic antibiotics to control growth of microorganisms on and around the device during use.

An alternative approach is the production of devices that possess broad spectrum antimicrobial activity. A variety of approaches have been taken to endow devices with antimicrobial properties including soaking of indwelling catheters and other devices in antibiotics such as penicillin or fluconazole, or in antiseptic solutions such as chlorhexidine or sulfadiazine. Although these approaches render some antimicrobial activity to the devices, they are of limited utility due to toxicity, stability and effectiveness. Such limitations include short half-lives in tissue or on the devices, the agents' spectrums of activity are too narrow for the range of organisms that may be encountered near the device, or the agents may be destructive to tissues at their effective concentrations.

Heavy metals may provide an optimal alternative as antimicrobial agents for rendering medical devices with antimicrobial properties. Heavy metals may exist as salts, complexes with carriers, as base metals or other forms. This versatility contributes to the variety of ways in which the forms can be coupled with the devices. In addition, it is known that heavy metals such as gold, platinum, silver, zinc and copper exert antimicrobial activity at very low concentrations against a broad spectrum of organisms including bacteria, protozoa, fungi and viruses (N. Grier, "Silver and its compounds" In Disinfection, Sterilization, and Preservation, ($3^{rd}$ edition S. S. Block, ed., Lea & Febiger, Philadelphia, Ch. 20, (1983).). Silver is oligodynamic, meaning that it has antimicrobial activity at very low concentrations against a wide range of bacteria, fungi and viruses. Measurements of ionic silver as low as $10^{-6}$ to $10^{-9}$ M have been shown to be antimicrobial (A. D. Russel and W. B. Hugo, "Antimicrobial Activity and Action of Silver", Prog. in Med. Chem. 31:351–370, 1994.) Moreover silver is well tolerated by mammalian cells and tissues.

One active heavy metal, in particular silver, has long been recognized for its broad spectrum anti-microbial activity and compatibility with mammalian tissues. Although silver has been used in a large range of medical devices, its incorporation, as a prophylactic anti-infective agent, in primary wound contact products has been restricted due to silver's adverse properties. These properties include a short half-life, the rapid inactivation of silver by protein, and light-mediated discoloration of the product containing silver and any body parts touching the product, such as skin. Recently, manufacturers have tried methods to overcome some of the limitations to broaden the utility of silver in wound care. The currently available silver-containing wound care dressing materials have been unsuccessful in adequately overcoming the problems inherent in using silver.

The mode of action of silver is due to the reactivity of the ionic form with a variety of electron donating functional groups that contain reactive entities such as oxygen, sulfur or nitrogen. Electron donating functional groups in biological systems are many and varied, including groups such as phosphates, hydroxyl, carboxylates, thiol, imidazoles, amines, and indoles. Microbial macromolecules are richly endowed with these functional groups that, when bound by silver ion, may become inactivated and disfunctional resulting in the death of the microorganism. Ionic silver is known to disrupt microbial cell wall, cell membrane, electron transport, metabolic and anabolic enzymes, and nucleic acid function (A. D. Russel, W. B. Hugo, "Antimicrobial activity and action of silver" In Progress in Medicinal Chemistry. Vol. 3, G. P. Ellis & D. K. Luscombe, ed., Elsevier Science B. V., (1994)).

Oligodynamic silver has been incorporated into medical inventions for the purpose of imparting an antimicrobial effect. The use of metallic silver was reported in UK patent application No. 2134791A which describes the vapor deposition of metallic silver or silver/carbon on Sphagnum moss for the purpose of making an antimicrobial surgical dressing. U.S. Pat. No. 5,753,251 describes the production of a wound contact product by sputter coating silver on to substrates such as plastic films to impart antimicrobial activity to the device. A description of a metallized bandaging material, prepared by vapor coating metallic silver onto a fiber fleece was described in U.S. Pat. No. 2,934,066. U.S. Pat. No. 4,483,688 describes the combining of finely ground metallic silver with a binding agent for coating indwelling catheters.

Alternative means of incorporating silver or silver salts into or on devices have also been described. The incorporation of antimicrobial silver into the adhesive of an adhesive coated, moisture impermeable thin film polymer for use for securing medical devices or as a wound dressing was described in U.S. Pat. No. 4,340,043. The use of silver oxide, finely ground into small particles, dispersed in latex batching has been described in U.S. Pat. No. 4,902,503 for use in making indwelling medical devices where antimicrobial activity would increase effectiveness.

Although these devices have provided certain solutions to combining antimicrobial activity with medical devices, these inventions have identified a number of limitations associated with silver and silver salts. The highly reactive nature of silver ions contributes to the relatively short half-life of the antimicrobial effect in the presence of certain functional groups. Moreover its antimicrobial form, ionic silver, is unstable in light and is rapidly converted to a black inactive precipitate by photo-reduction.

Attempts at overcoming the limitations of silver addition included applying silver or silver salts onto dry substrates where little or no ionization of silver could occur or the use of substrates containing few reactive functional groups that would react with ionic silver. However, this is impractical for applications where moisture abounds such as in moist devices such as soft contact lenses, hydrated plastic implants, or in moist wound dressing cover such as a hydrogels, hydrocolloids, or biologics, or in medical devices that contain reactive functional groups such as in a collagen matrix.

To overcome these problems, inventions describing stabilization of silver have been described. U.S. Pat. No. 5,863,548 describes the process of forming a complex between silver and allantoin which in turn is encapsulated in allantoin to form a light stable antimicrobial coating for medical devices. U.S. Pat. No. 5,709,870 describes a process for producing a light and heat stable silver complex with carboxymethyl cellulose for use in coating fibers. Similarly U.S. Pat. No. 5,744,151 describes a process for rendering silver photo-stable and antimicrobial for use as an adjunct to pharmaceuticals by forming an acyclic polyether polymer stabilized by ratios of cation and anions in the process.

The stabilization of the antimicrobial effect of silver in a device that is exposed to light or is in contact with functionally reactive groups may also be accomplished by retarding the release of the silver ion into the environment around the device after application. In other words by using mechanisms that continuously release a small steady supply of ionic silver into the device. An invention described in U.S. Pat. No. 5,470,585 incorporates silver into a form of glass that slowly dissolves in the presence of moisture. The slow dissolution of the matrix thereby releases ionic silver about the device. Sputter coated nanocrystalline silver coatings on devices such as plastics for wound care initially are similarly slowly released from the device during contact with moisture of tissues to liberate ionic silver around the device during use as is described in U.S. Pat. No. 5,753,251.

These inventions have provided some solutions to the problems of stability, and half-life for silver for several silver antimicrobial applications. However they are cumbersome, may contain toxic accessory agents that support function, or are prohibitively expensive for application to commodity medical devices such as wound dressings. Moreover, these approaches are not solutions to the incorporation of antimicrobial silver into devices that contain solvents where ionization of the silver would normally occur in wound dressings such as hydrogels, moist contact lenses, oral prosthetics and other devices containing water. In addition, these inventions make only marginal contribution to the sustained continuous release of ionic silver from devices treated by the processes described. What is needed are compositions and methods for providing antimicrobial activity in medical devices, and particularly for silver incorporation into medical devices such as moisture-containing wound dressings, skin contact devices, such as monitor leads, wound dressings and hydrated plastic implants.

SUMMARY OF THE INVENTION

The present invention comprises compositions and methods for producing materials that contain stabilized antimicrobial metals, preferably silver, for many uses, including medical products. In particular, the present invention provides methods and compositions for administering active agents, such as antimicrobial silver, to the site of a wound via wound dressings. The present invention also allows for localized delivery of active agents and prevents the negative effects of system-wide administration. The present invention comprises wound healing devices that have specialized structures that aid in treatment of wounds.

A preferred embodiment of the present invention comprises a hydratable matrix material that has an antimicrobial agent, such as a heavy metal, most preferably, silver, incorporated into the matrix. The matrix preferably also comprises components that stabilize and control the release of the active agent into the surrounding environment when used.

In a preferred embodiment of the present invention, active agents are incorporated directly, or may be incorporated by sequentially adding components or precursors of the active agent to the matrix of the devices, and having the precursors form the active form of the active agent in or on the matrix. The agents may be incorporated by absorption or adsorption of agents or precursors by the matrix, and preferably by incorporation during the polymerization of the matrix. It is theorized that the release of the active agents may be controlled via manipulation of concentration parameters, movement of water through the matrix and the degree of cross-linking in the matrix. In another preferred embodiment, the wound dressings comprise a stranded configuration, wherein the strands extend from at least one common region and the strands themselves comprise a polymer matrix.

The wound dressing devices of the present invention may be used to simultaneously deliver a number of active agents to a wound site. Wound healing agents such as antimicrobial agents, antifungal agents, antiviral agents, growth factors, angiogenic factors, anaesthetics, mucopolysaccharides and other wound healing proteins may be incorporated into the wound dressings for controlled release. Adjuvants and other agents, such as those that boost the immune system, may also be incorporated into the wound dressings devices of the present invention. A surprising and novel aspect of a preferred embodiment having agents directly incorporated into micro-cavities of the matrix is that the activities of the wound healing agents are not altered by incorporation into the devices and that the agents are effective upon their release.

In a preferred embodiment of the present invention, the wound dressing devices of the present invention comprise a novel stranded structure made from a matrix suitable for application to broken skin and underlying tissues. The individual strands of the preferred embodiment may or may not have free floating ends, however, the unique arrangement of the device allows it to both absorb excess wound exudate, and simultaneously conform closely to the walls of the wound bed, in order to accelerate overall wound healing.

A stranded configuration of the wound dressings of the present invention is particularly desirable because the novel design provides a high surface area to volume ratio to maximize interchange between the matrix and wound moisture and wound debris. The multiple strands of the preferred configuration provide maximal inter-strand space to serve as a reservoir for moisture, necrotic materials, or agents scheduled for delivery to the wound bed. The superior moisture absorption and regulation capacity of the preferred embodiment equip the wound dressing devices for use on heavily to moderately draining wounds.

In addition to increased moisture absorption and the ability to deliver active agents, the individual strands of the preferred configuration may participate in mechanical debridement thereby accelerating the wound healing process. The individual strands of the preferred wound dressings increase the inherent flexibility of the device, and enhance conformability to the irregularities of the contours in the wound cavity, allowing the preferred devices to be used in deeply cavitated wounds where debridement is essential. In order to simplify the overall wound dressing procedure, the preferred devices may have a single unit construction that is applied and removed as a complete unit, leaving no remnants. Additionally, the preferred devices may be left in place for prolonged periods between changes.

Other forms of the matrices of the present invention, such as molded articles, are also contemplated by the present invention. Other forms also include films, sheets, fibers and amorphous gels. The matrices of the present invention can be dipped or applied in methods known to those skilled in the art to articles or devices.

A preferred embodiment of the present invention comprises methods and devices that incorporate antimicrobial agents, more preferably, the agents are heavy metals, and most preferably, the agents are silver compositions. The silver-containing devices have antimicrobial activity, are resistant to light degradation, possess sustained release characteristics, and provide improved wound healing ability. Methods of the present invention comprise methods for making the antimicrobial devices, such as wound dressings, and methods of use of such devices.

Another preferred embodiment of the present invention comprises devices and methods for making and using such devices that comprise materials that allow for the application and stabilization of antimicrobial metals such as silver. Preferred embodiments comprise devices made with or associated with hydrophilic pre-formed fibrous materials. A preferred use is for use in medical and non-medical devices and materials for the purpose of imparting sustained, light stable antimicrobial activity to the device. In particular, the present invention relates to compositions and methods for the incorporation and stabilization of silver onto and within the hydrophilic fibers of cross-linked and non-cross-linked celluloses such as carboxymethy cellulose and hydroxymethyl cellulose, cotton, rayon, and of fibers made from polyacrylates and other synthetic and natural polymers, and fibers of calcium alginates that may be used as a primary contact sustained-release silver antimicrobial materials.

Additionally, the methods of incorporating stabilized heavy metals, particularly silver, into materials can be used for a wide variety of products. For examples, such methods include adding antimicrobial characteristics to cosmetic products, such as dressings, topical lotions, or compresses for acne and blemishes, scar reduction, tattoo removal, and laser resurfacing, any body- or skin-contacting medical devices, such as, catheter coatings, guidewire coatings, ostomy appliances, respiratory and feeding appliances, contact lenses, and hearing aids; and personal and skin care products, such as skin conditioners, barrier creams, lubricating preparations, and super absorbents for addition to diapers, adult incontinence products, and feminine hygiene products.

Accordingly, it is an object of the present invention to provide compositions and methods for the treatment of wounds.

Another object of the present invention is to provide compositions and methods that facilitate and accelerate the wound healing process.

Yet another object of the present invention is to provide a wound dressing device wherein active agents are incorporated.

It is another object of the present invention to provide wound dressing devices that absorb excess moisture at a wound site.

It is another object of the present invention to provide wound dressing devices that promote autolytic debridement.

Yet another object of the present invention is to provide a wound dressing device that absorbs wound exudate by allowing for optimal contact between the device and the wound area.

A further object of the present invention is to provide wound dressing devices for external and internal wounds.

Another object of the present invention is to prevent infection by providing wound dressing devices that clean wound sites by removing debris and contaminating material.

It is another object of the present invention to provide wound dressing devices that easily conform to the shape of a wound.

It is yet another object of the present invention to provide wound dressing devices that are easily manufactured.

Still another object of the present invention is to provide wound dressing devices that may be easily removed from wounds and replaced.

Yet another object of the present invention is to provide wound dressing devices that are compatible with injured tissue and do not induce irritation or inflammation.

It is yet another object of the present invention to provide wound dressing devices that function to both absorb wound exudate and promote autolytic debridement.

Another object of the present invention is to provide methods and compositions for making single unit construction wound dressing devices having multiple strands.

It is another object of the present invention to provide methods and compositions for treating wounds using wound dressing devices that function to both absorb wound exudate and deliver wound healing agents.

An object of the present invention to provide methods and compositions for treating wounds using wound dressing devices having active agents incorporated therein.

Still another object of the present invention is to provide methods and compositions for delivering active agents to wound sites and damaged tissue.

An object of the present invention comprises methods and compositions for providing devices with antimicrobial activity.

Another object of the present invention comprises methods and compositions for providing moisture-containing devices with antimicrobial activity.

Still a further object of the present invention comprises methods and compositions for providing devices that are essentially dry with antimicrobial activity.

These and other objects, features and advantages of the present invention will become apparent after a review of the following detailed description of the disclosed embodiments and the appended claims.

BRIEF DESCRIPTION OF THE FIGURES

FIG. 1 is a three dimensional view of one embodiment of a wound dressing device of the present invention wherein the multi-stranded device may have free floating strand ends.

FIG. 2 presents a cross-section of a strand of the multi-strand device.

FIG. 3 is an illustration of a pattern of a die used for cutting a device from an appropriate matrix material.

FIG. 12 is a graph showing the effect on the bioburden when using a silver-containing device.

DETAILED DESCRIPTION

Figure 4:
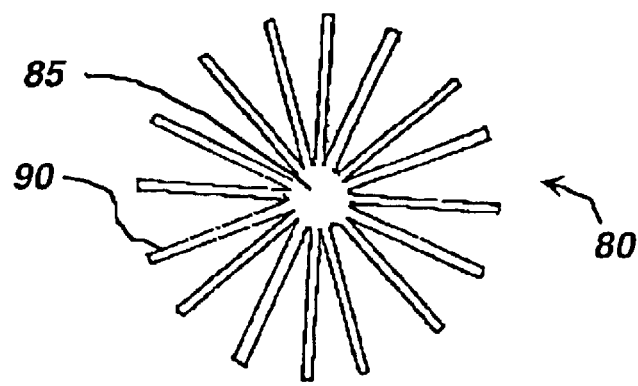
FIGS. 4–7 illustrate additional embodiments of a wound dressing device.

The present invention comprises compositions and methods for making and using materials comprising antimicrobial activity. Such materials may be hydrophillic moist materials or dry materials. In particular, the present invention comprises compositions and methods for making and using such materials, for example for treating wounds using wound dressing devices with active agents incorporated therein. A preferred active agent is silver that is incorporated into the materials and is stabilized until released by application or placement in the site of use. In a preferred embodiment, the active agents may be directly incorporated into the scaffolding matrix of the devices for controlled release at the site of the wound. In a further preferred embodiment, the matrix comprises a biocompatible, scaffolding polymer network, such as a polyacrylate hydrophillic polymer, with a non-gellable polysaccharide dispersed evenly throughout said network. Most preferably, the matrix has antimicrobial activity associated with it The matrices of this preferred embodiment provide a reliable and efficient means for delivering active agents to the site while at the same time may also provide a superior moisture regulation capacity which is important for promoting wound healing.

The wound dressing devices of the present invention are preferably in the form of a continuous sheet form, similar to wound dressings known in the art. However the invention may also take other particular conformations. For example, a preferred embodiment of the present invention comprises a stranded configuration wherein the individual strands extend from at least one common region and may have free-floating ends. This particular conformation is particularly suitable for use in deeply cavitated wounds since the multiple matrix strands enable the dressing to conform to individual and uniquely shaped wound areas. Furthermore, the devices accelerate wound healing by displacing and allowing for the removal of excess cellular exudate and debris, thereby improving the rate of tissue repair and regeneration.

The terms "a", "an" and "the" as used herein are defined to mean one or more and include the plural unless the context is inappropriate.

Active Agents

The active agents incorporated into the matrices and devices of the present invention may be used for a variety of applications where there is a need for the presence of the active agent. A particularly preferred use is in the treatment of wounds or in skin healing. The active agents may participate in, and improve, the wound healing process, and may include antimicrobial agents, including but not limited to antifungal agents, antibacterial agents, anti-viral agents and antiparasitic agents, growth factors, angiogenic factors, anaesthetics, mucopolysaccharides, metals and other wound healing agents.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, heavy metals including, but not limited to, gold, platinum, silver, zinc and copper, and their combined forms including, salts, such as chloride, bromide, iodide and periodate, and complexes with carriers, and other forms.

Growth factor agents that may be incorporated into the wound dressing devices of the present invention include, but are not limited to, basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors α and β (TGF-α and TGF-β), interleukin-8 (IL-8); granulocyte-macrophage colony stimulating factor (GM-CSF); the interleukins, and the interferons.

Other agents that may be incorporated into the wound dressing devices of the present invention are acid mucopolysaccharides including, but are not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins that may be especially useful in the treatment of wounds include, but are not limited to, collagen, cross-linked collagen, fibronectin, laminin, elastin, and cross-linked elastin or combinations and fragments thereof Adjuvants, or compositions that boost an immune response, may also be used in conjunction with the wound dressing devices of the present invention. Antibodies or antibody fragments are also included.

It is to be understood that in a preferred embodiment of the present invention, the active agent, more preferably heavy metals, most preferably silver, is incorporated into the matrices or devices so that the agent is released directly from the devices and delivered to the contact substrate such as the wound site or application site. The incorporated agents may be released over a period of time, and in this way, the devices retain their ability to kill or inhibit microorganisms over an extended period of time. As used herein, the term silver includes all silver salts or silver compounds, including, but not limited to, silver chloride, silver phosphate, silver sulfate, silver iodide or silver bromide. The active form of the silver salt is the silver ion, as is the case for the active forms of the heavy metals.

Administering active agent for the prevention or control of local infection using the wound dressing itself overcomes several of the problems of the prior art. First, the present invention avoids the painful re-application of salves and ointments to the wound. The present invention also allows silver to be delivered directly into the site of the wound to prevent the negative impact of system wide delivery of the agents as encountered after oral or intravenous administration. In the case of deeply cavitated wounds, in contrast to the topical application of active agents, the wound dressing and silver therein may be located directly within the wound, providing a more effective delivery of the agents. Finally, in contrast to an injection of active agents, the present invention provides methods of administering active agents wherein the agents may be removed immediately from the wound and the administration terminated.

Matrices

The devices of the present invention comprise a hydrophilic matrix material, preferably, one that is flexible and elastic, and is of a semi-solid scaffold that is permeable to substances such as inorganic salts, aqueous fluids and dissolved gaseous agents including oxygen. The substances permeate the matrix through movement via intermolecular spaces among the cross-linked polymer. The matrix may be moist or dry.

Preferably, the hydrophilic matrix material is constructed from a natural or synthetic polymer and a non-gellable polysaccharide. Natural hydrophilic polymers that may be used for the construction of the wound device include, but are not limited to collagen, animal hide, hyaluronic acid, dextran and alginate. Additionally included are hydrophilic fibers of cross-linked and non-cross-linked celluloses such as carboxymethy cellulose and hydroxymethyl cellulose; cotton, rayon, and of fibers made from polyacrylates; and fibers of calcium alginates that may be used as a primary contact sustained release silver antimicrobial material. Synthetic polymers that may be used include, but are not limited to polyacrylamide, polyvinyl's (PVP, and PVC), polyacrylate, polybuterate, polyurethane foam, silicone elastomer, rubber, nylon, vinyl or cross linked dextran. If cross-linked dextran is used, it is preferred that the molecular weight of the dextran polymer is between 50,000 and 500,000. The most preferable non-gellable polysaccharide is a non-gellable galactomannan macromolecule such a guar gum. A range of guar gum between approximately 0.01 kg to 100 kg, preferably between approximately 0.1 kg to 10 kg, and most preferably between approximately 0.5 kg to 2 kg is generally sufficient. Other non-gellable polysaccharides may include lucerne, fenugreek, honey locust bean gum, white clover bean gum and carob locust bean gum.

To decrease the permeability of wound dressing devices comprising a cross-linked polymer and non-gellable polysaccharide matrix, water loss control agents may be applied to the surface of the device. Application of water loss control agents is preferred since a decrease in the permeability of the device controls the loss of fluids from the wound. The preferred water loss control agent is petrolatum, however, other water loss control agents such as glycolipids, ceramides, free fatty acids, cholesterol, triglycerides, sterylesters, cholesteryl sulfate, linoleic ethyl ester and silicone oil may also be used.

If desired, a plasticizer may also be added to the matrix material. A preferred plasticizer is glycerol and water, however, propylene glycol and butanol may also be used. If glycerol is used, a range of between approximately 0.5 kg to 50 kg, preferably between 1 kg and 30 kg, and most preferably between approximately 5 kg to 15 kg is generally sufficient. The plasticizer may be added in the initial mixture of polymer and cross-linking agent.

If desired, a hydration control agent may be incorporated into the matrix. The preferred hydration control agent is an isopropyl alcohol, however, ethanol, glycerol, butanol, and propylene glycol may also be used. A range of isopropyl alcohol of between approximately 0.1 kg to 10 kg, preferably between approximately 0.2 kg to 5 kg and most preferably between approximately 0.5 kg to 2 kg is generally sufficient.

The matrix of the preferred embodiment preferably comprises polymerized chains of acrylamide monomer, wherein the acrylamide monomers are cross-linked with a cross-linking agent, a non-gellable polysaccharide, and an active agent or pharmaceutical directly encapsulated into microcavities therein. A range of acrylamide between approximately 1 kg to 100 kg, preferably between approximately 2 to 50 kg, and most preferably between approximately 5 kg to 20 kg is generally sufficient. A preferred matrix comprises a cross-linked polyacrylamide scaffolding that enmeshes guar gum as disclosed in U.S. Pat. No. 5,196,160 to Nangia.

The most preferable cross-linking agent is NNNN'-methylenebisacrylamide, however other appropriate cross-linking agents such as bisacrylylycystamine and diallyltartar diamide may also be used. If NNNN'-methylenebisacrylamide is used, a range of between approximately 0.01 kg to 1 kg, preferably between approximately 0.02 kg to 0.5 kg, and most preferably between approximately 0.05 kg to 0.3 kg is generally sufficient. As noted above, the most preferable non-gellable polysaccharide is a non-gellable galactomannan macromolecule such a guar gum, but other non-gellable polysaccharides may include lucerne, fenugreek, honey locust bean gum, white clover bean gum and carob locust bean gum.

Ammonium persulfate and TEMED may also be added to the matrix. A range of ammonium persulfate between approximately 0.01 kg to 1 kg, preferably between approximately 0.02 kg to 0.5 kg, and most preferably between approximately 0.05 kg to 0.2 kg is generally sufficient. Additionally, a range of TEMED between approximately 0.01 kg to 1 kg, preferably between approximately 0.02 kg and 0.5 kg, and most preferably between approximately 0.05 kg to 0.3 kg is generally sufficient.

Incorporation of Active Agents

One embodiment of the matrices of the present invention can be found in U.S. Pat. No. 5,196,190 to Nangia et al., which is hereby incorporated in its entirety. Nangia et al. teach a matrix composed of a natural or synthetic polymer, a non-gellable polysaccharide, and a phospholipid-based drug delivery system. In particular, Nangia et al. teach a matrix capable of drug delivery, wherein lipid vesicle liposomes containing a desired drug are incorporated into the matrix.

One problem with the prior art methods, however, is the difficulty of incorporating active agents into the liposomes since some agents may be incompatible with liposome chemistry. Incorporation using liposomes is time consuming, expensive and sometimes unreliable because dispersion of the liposomes in the matrix is difficult to achieve and once achieved, the liposomes may prematurely release costly agents due the liposomes' inherent instability. Another problem is that the prior art fails to teach a method of incorporating active agents into a wound dressing wherein the release of the agent over time can be controlled through the manipulation of concentration parameters, movement of water through the matrix and the degree of cross linking in the matrix.

Preferred embodiments of the present invention however, address the need for a less expensive, quicker, and more reliable method for incorporating a wider range of desired agents into matrices and devices. Preferred embodiments also provide a means to control the release of the desired agents over time via manipulation of concentration parameters, movement of water through the matrix and the degree of cross-linking in the matrix. In a preferred embodiment, the desired agents may be directly incorporated into the matrix by adding the agents into the initial formulation for the matrix prior to cross-linking. This method of incorporation is inexpensive, rapid and reliable, and most surprisingly, the incorporated agents are not affected by the process of polymerization and retain their biological activities. Another preferred method of incorporation is the adsorption or absorption of solutions containing the active agents or precursors of the active agent to an already formed matrix.

Using preferred embodiments of the present invention, delivery of the desired agents may be controlled by the use of movement of liquid through the matrix. Though not wishing to be bound by any theory, it is theorized that the liquid in a matrix of polymer and non-gellable polysaccharide is either bound to the non-gellable polysaccharide or it is unbound in the polymer mass. Thus, it is theorized that the present invention uses the free liquid portion of the matrix as a general solvent and as a means to deliver desired agents. Soluble drugs are easily dissolved in the free liquid portion, however slightly soluble drugs are ground to a fine powder and may require the use of a wetting agent such as glycerol or isopropyl alcohol or a surfactant such as polysorbate, triton-X or sodium lauryl sulfate.

Once the desired active agent or agents are dispersed throughout the matrix, a portion of the agent resides in the non-gellable polysaccharide, while another portion of the agent is dissolved in the free liquid phase and moves freely through the matrix. The ability of the agent to move freely throughout the matrix in the free liquid phase is important in the agent delivery system of the present invention. Because the agent is dissolved in the free liquid phase, a concentration gradient of the active agent is created between the matrix of a wound dressing device and the moisture of the wound itself. Therefore, when the matrix is placed onto a moist surface such as an open wound, the soluble agent will move through the free liquid phase toward the agent-free wound moisture, resulting in the delivery of the agent to the wound. This movement of soluble agent further upsets the equilibrium between soluble and insoluble agents, and causes more agent to dissolve into the free liquid phase, thus causing more agent to be delivered to the wound. Because the present invention incorporates the desired agent directly into the matrix rather than incorporating the drug into other delivery vehicles, such as liposomes, the agent may be dissolved in the free liquid phase and reliably delivered to the wound through the process described above.

Delivery of the desired agents may also be controlled by the degree of cross-linking in the matrix. As described above, the desired agents may be added to the other ingredients forming the matrix prior to the addition of the cross-inking agent. Subsequent addition of the cross linking agent and concomitant polymerization results in both chain elongation of monomeric chemicals and cross-linking between chains of monomers. The combination of chains cross-linked together creates micro-cavities wherein the desired agents are encapsulated. By controlling the amount of cross-lining agent and the length of chains of monomer, it is possible to regulate the size of the micro-cavities in the polymer. Larger micro-cavities, produced by a lower degree of cross-linking, allow for freer migration and quicker delivery of the desired agent, whereas smaller micro-cavities increase the delivery time. Although the liposome based delivery system may also make use of the degree of cross-linking, the liposome itself acts as an additional barrier to delivery, making delivery less controlled and less reliable.

The present invention comprises compositions that are useful for stabilization of heavy metals, particularly silver, for devices that have sustained release characteristics, are light stable, and possess antimicrobial activity. In particular, this invention relates to the incorporation and stabilization of silver salts into a hydrated polyacrylate matrix that may be used as a primary contact sustained release silver antimicrobial material for use in wound dressings and other devices and materials.

The polyacrylate matrix as taught in the Nangia patent, U.S. Pat. No. 5,196,190., has little or no antimicrobial properties when applied to wounds. A preferred embodiment of the present invention comprises the incorporation of antimicrobial silver into the matrix to increase its effectiveness and utility for application such as in wound care where microbial growth may inhibit or complicate the wound healing process. The preferred polyacrylate matrix, like many hydrated medical devices, contains a significant amount of aqueous moisture. This moisture serves as a solvent in which many of the undesirable characteristics of silver are exhibited. These include the formation of ionic silver which is highly reactive to functional groups that exist on organic material that may be part of the device; the formation of the photo-reactive form (Ag+) of silver that may lead to discolorization; a solvent phase that contributes to the instability of silver to certain levels of heat; as well as the transfer of antimicrobial silver to adjoining packaging materials through migration of silver through the solvent phase. Preferred methods and devices of the present invention comprise addition of compositions comprising metals, preferably silver, that are added to hydratable medical devices such as hydrogels to provide stable sustained release antimicrobial activity.

The present invention contemplates devices comprising metals, and a preferred metal is silver. Though silver is taught as a preferred embodiment, the present invention comprises use of any metal that imparts antimicrobial activity to a matrix or device. It has been found that silver salts such as silver chloride are generally stable in the salt form. Moreover, many silver salts such as silver phosphate and silver sulfate are only weakly soluble in aqueous solvent. Methods of the present invention comprise preparing a salt of silver during the preparation of the matrix, and preferably the matrix is a hydratable polyacrylate polymer.

The formation of the weakly soluble salt, silver chloride, is fully dispersed throughout the matrix and provide the precursor for the formation of the sustained release silver. The deposition of collodial silver chloride or other weakly soluble salt throughout the matrix is accomplished by any one of several methods of the present invention. In one method, the preformed salt, such as silver chloride, may be incorporated along with other components during the compounding of the matrix formulation prior to polymerization. Another method comprises sequentially adsorbing or absorbing solutions comprising the precursor components, such as weakly soluble salts into a matrix. For example, a solution containing chloride ions is added to a polymerized hydrophilic matrix, where the solution is adsorbed or absorbed by the matrix. A second solution, containing silver ions, is added to the matrix to form a colloid of silver chloride in the matrix. Another method, and a preferred method, is the sequential addition of anions and cations during the compounding of the material mixture, causing the formation and dispersion of the colloid in the mixture prior to polymerization.

Preferred chloride ions comprise any dissociable salt, including, but not limited to, sodium chloride, potassium chloride, copper chloride, ferric chloride, zinc chloride calcium chloride and hydrochloric acid. Such chloride ions may be added in solution or dry form.

An ionic silver solution comprises compositions such as those prepared by dissolving a salt of silver, including but not limited to silver nitrate, silver acetate, silver citrate, and silver sulphate, into water. The silver ions may also be added in a dry form.

When the polymer is catalyzed to gel, the finely dispersed silver chloride is immobilized within the polymer where it undergoes disassociation (as an example according to the formula):

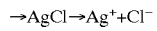

$$\rightarrow AgCl \rightarrow Ag^+ + Cl^-$$

Since AgCl is only weakly soluble in aqueous solutions the re-association to AgCl is strongly favored. However the ionic form is unstable and may react to light to form insoluble elemental silver ($Ag^\circ$). This form has minimal antimicrobial activity and moreover is a black precipitate that strongly discolors the matrix when it is formed. In addition the ionic form ($Ag^+$) is highly reactive with functional electron donating groups which may reduce its antimicrobial effect. Therefore it is desirable to stabilize the silver in hydrated polymers such as the preferred embodiment, by providing an excess of chloride ions in the matrix to favor association rather than disassociation.

Although excess chloride ions in the matrix provide conditions that favor the formation of the stable silver chloride salt form of silver, an amount of free ionic silver exists in the matrix. The ionic form ($Ag^+$) may react with electron donors leading to a steady conversion of ionic silver into non-antimicrobial forms and left to continue would significantly deplete the matrix of a source of antimicrobial silver. The reaction of ionic silver with strong electron donating groups such as light, can be inhibited by the incorporation of a competing electron acceptor that has a higher electrochemical potential than silver in the matrix. In the preferred embodiment, either ionic copper or ionic iron are both strong electron acceptors that may be incorporated into the matrix to stabilize ionic silver in the matrix until it is applied to a moist environment such as a wound. The electron acceptors are added to the matrix solution in a stabilizing solution. A stabilizing solution is a solution that provides components, including but not limited to the electron acceptors, that aid in the prevention of the reaction of the active agent. For example, in a preferred embodiment, a stabilizing solution comprises a solution of electron acceptors such as a copper chloride or ferric chloride solution, for addition to a silver-containing matrix mixture to aid in the prevention of the reaction of ionic silver. Alternatively, a stabilizing solution also comprises the addition of electron acceptors, such as copper chloride or ferric chloride, in a dry form, not in a liquid solution. Additionally, a stabilizing solution comprises one or more electron acceptors for prevention of reaction of the active agent.

Other electron acceptors that can be used in the present invention include, but are not limited to, gold, platinum and cesium. Other strong organic oxidizers may be used to prevent the reduction of ions, such as the reduction of silver by light energy.

A preferred embodiment of the present invention comprises a wound healing device comprising a polyacrylate hydratable matrix produced according to U.S. Pat. No. 5,196,190 with antimicrobial properties provided by incorporating heavy metals, preferably silver. Other preferred embodiments comprises devices that are coated with matrices, preferably a biocompatible polymeric matrix comprising a scaffolding polymer network with antimicrobial activity. A non-gellable polysaccharide may or may not be included with the matrix.

A silver containing polyacrylate matrix generally comprises mixing approximately 100–250 g acrylamide and approximately 0.5 to 5.0 g bisacrylamide into 2800 to 3950 g of water containing between 6 to 54 g of sodium chloride. To this mixture, add 21 g of guar gum and 188 g of glycerol.

After mixing to homogeneity, slowly add an aqueous solution containing approximately 0.01–3.1 g silver nitrate to the mixing batch. Alternatively, molar equivalents of silver acetate, silver citrate or silver sulfate may be substituted for silver nitrate. After formation of the finely dispersed silver complex, dissolve either from about 0.1 to 2.8 g copper chloride ($CuCl_2$) or about 0.3 to 3.3 g ferric chloride $FeCl_3$. Alternatively, molar equivalents of potassium chloride, magnesium chloride, zinc chloride, calcium chloride, hydrochloric acid or other soluble chloride salt may substituted for the ferric or copper chloride. The polymerization of the mixture into a polymer is accomplished by blending approximately 0.7 to 3.6 ml TEMED and about 0.2 to 4.6 g ammonium persulphate into the mixture. The mixture is poured into the appropriate molds with the desired shape before polymerization in a dark place. The gelled polymer is typically removed from the mold, dehydrated by mild heat in a darkened drier and then rehydrated by humidification to a desired moisture content, approximately 15 to 50% w/w. The matrix may cut into a desired size or shape, packaged and then is sterilized by irradiation with an electron beam or gamma irradiation.

The present invention also comprises compositions and devices comprising preformed hydrophillic fibers and methods for making and using such materials with antimicrobial activity. Pre-formed cross-linked hydrophilic fibers have been shown to have utility in wound care due to their absorbency of wound fluid and their compatibility with exposed tissues. Many hydrophilic fibrous materials are readily available through commercial channels for on-processing, packaging and sterilization for use in wound and other medical applications. However none of these materials are available with silver impregnation due to the instability of silver and due to the lack of effective known methods for the incorporation of stabilized silver into the substrates of these materials prior to fiber formation. Furthermore these materials have little or no inherent antimicrobial activity. Therefore the most practical method for rendering these materials antimicrobial would be the application of silver in a stabilized form to the pre-formed fibers. U.S. Provisional Patent Application No. 60/157,000, herein incorporated in its entirety, describes a method of incorporation of antimicrobial silver into materials, preferably polyacrylate materials, by the formation of a silver chloride colloidal precipitate during the compounding of the matrix material. The silver complex was stabilized by a combination of excess copper and chloride ions. The incorporation of a stabilized form of silver colloid into pre-formed hydrophilic fibrous materials is impractical. Therefore this invention also comprises methods for the incorporation of silver into fibrous materials by an impregnation method that causes the in situ formation of a stabilized silver colloid complex within and around the fibrous material.

One method of making materials with antimicrobial activity is to disperse a chloride salt of sodium or copper or iron in water at a concentration that remains in solution when the water is combined with an alcohol solvent, including, but not limited to, isopropyl alcohol and ethanol. The fibrous matrix materials for impregnation are then immersed in a bath of the chloride ions so that the material is completely immersed. After a suitable time the material is then removed and blotted of excess chloride-containing solvent. Then the material is immersed in a similar aqueous/alcohol bath that contains silver and copper or iron ions. After a suitable time, the material is removed, blotted of excess reagent and air dried. It is desirable that the ratio of water to alcohol in mixtures that contain the ionic elements not exceed a concentration that would cause hydrophilic materials to begin to gel. A preferred range comprises 5–15% aqueous, it is highly preferred that the aqueous portion not be greater than 50%. Reversal of the immersion sequence is inconsequential to the success of impregnation of the fibrous materials.

An alternative method for the impregnation of the silver compound is to combine the silver ion and chloride ion into an aqueous component of an alcoholic solvent bath along with copper or ferric ions before immersion and soaking of the fibrous materials. Thereafter the fibrous materials should be removed, blotted and air dried to form a stable antimicrobial material for application to wounds and other compromised tissues.

It has been found that silver salts such as silver chloride are generally stable in the salt form. Moreover many silver salts such as silver chloride, silver bromide, and silver iodide as examples, are only weakly soluble in an aqueous environment. Therefore the present invention comprises methods of preparing a weakly soluble salt of silver on and within the filaments of the hydrophilic material during the process and is specifically one object of the invention. The formation of the weakly soluble salt, such as silver chloride is done by sequentially localizing the ions of the salt within the hydrophilic material. This is accomplished by using the aqueous portion of the aqueous-alcohol solvent bath as the delivery vehicle which is selectively absorbed by the material due to its hydrophilic properties. It is possible that some delivery of ionic species is accomplished also by the permeation of the alcohol carrying ions into the matrix as well. The coincident location of the silver and chloride ions in the preferred embodiment result in nucleation of a colloidal-like structure within the matrix. The use of a bath that is predominately composed of an organic solvent such as alcohol or any other solvent that does not cause gelling or swelling of the fibrous materials is desirable. This is important in that it prevents the need for substantial dehydration of the fibrous materials following immersions as well as for allowing recovery, and re-use of the baths for treating other materials.

The nucleated silver salt within the matrix is immobilized and stabilized by the presence of excess chloride containing salts as well as copper or ferric ions, similar to the materials described above, to render the silver treated materials resistance to discoloration by light and radiation energy. The distribution of the nucleated silver salt is such that when the material becomes in contact with aqueous substrates such as wound fluid, there will be some solubilization of the silver salt thereby releasing silver ions which are antimicrobial. The rate of release is controlled by the inherent solubility of the silver salt, the amount of silver and the available moisture which are taken into consideration to provide sustained release of antimicrobial activity from the treated materials.

A preferred embodiment of the present invention comprises compositions of hydrophilic fibrous materials such as cross-linked carboxymethyl cellulose, calcium alginates and textiles such as cotton that have been impregnated by the methods of the present invention to form materials that possess antimicrobial activity which is released in a sustained manner over time and is stable to discoloration by light energy.

The antimicrobial matrices taught by the present invention can be formed into a variety of devices, especially preferred are those that polymerized polymers or plastics. Such matrices may also be coated onto devices to provide antimicrobial activity to the surfaces of such devices. The many uses of the compositions and devices of the present invention are not limited to the examples given here, but include polymeric matrices and their uses known to those skilled in the art. For example, the present invention contemplates using the matrices for adding antimicrobial characteristics to cosmetic products such as dressings, topical lotions, or compresses for acne and blemishes, scar reduction, tattoo removal, and laser resurfacing; to body contact medical devices(such as catheter and guidewire coatings, ostomy appliances, respiratory and feeding appliances, contact lenses, and hearing aids; and to personal and skin care products such as skin conditioners, barrier creams, lubricating preparations, and super absorbents for addition to diapers, adult incontinence products, and feminine hygiene products.

Stranded Structure

The devices of the present invention may take many physical forms, however, some preferred embodiments are constructed of thin strands of matrix suitable for placement into the wound bed or cavity. The preferred devices may be constructed from one or multiple strands of matrix. When multiple strands are used in the construction, the strands are secured together by wrap, tie, glue, or alternatively by a continuous bridge of matrix between adjacent strands. Multiple strands are secured together to minimize accidental loss during removal of the dressing from the wound bed. Typically, the strands of particular embodiments are bound or secured in the mid-region so that the ends of the device may float free. The advantage of free floating strands is to enable the individual strands to access a maximum volume of the wound and thereby absorb the excess fluid, exudate and debris. The mechanical action of the free floating strands contributes to the trapping and removal of cellular and wound debris. Concurrently the free floating strands also conform optimally with the contours of the wound surface to maximize contact between the device and the wound bed.

Referring now to the drawings, one preferred conformation of the wound dressing devices of the present invention is now described. This preferred conformation is useful for the control of exudate moisture accumulation, for stimulation of mechanical and autolytic debridement, and for delivery of active agents.

FIG. 1 is a three dimensional view of a preferred embodiment of the wound dressing device 10 with a strand 20 of the multi-strand device with free floating strand ends 40. The strands are secured together by a bridge 30 created during the cutting stage and composed of the matrix material used to construct the device. FIG. 2 represents a cross-section 22 of a strand 20 of the multi-strand device 10. It is intended that the cross-section 22 illustrate the sum of the linear dimensions of the sides. Preferably the sum of the linear dimensions of the sides is at least twice the numerical value of the surface area of the cross-section to provide an adequate surface area to volume ratio of the strands. More preferably, the sum of the linear dimensions of the sides is four or more times the numerical value of the surface area of the cross section.

FIG. 3 is an illustration of the pattern of a die 45 used for cutting a preferred embodiment of the wound dressing device 10 from an appropriate matrix material. Cutting blades 55, around the perimeter of the die, release the cut-out from the stock sheet of matrix during the cutting phase of production. Within the perimeter, a series of cutting blades 57 are situated lying parallel to one another extending from the ends of the pattern toward the center but not continuing through the center so as to leave a region 50 of uncut material in the center. The pattern of blades may vary according to the purpose of the wound dressing device. For example, the patterns may vary in terms of numbers of strands 20, numbers of regions of uncut region 50 for bridging strands, and the positioning of the single or multiple bridges 50 relative to the ends of the strands. The cross section 22 of the strands may be any suitable dimension that allows the appropriate interaction between strands and wound environment. The matrix may be any non-dissolving material that is suitable for contacting the broken skin, and underlying tissues including non-absorbent natural or synthetic materials, or absorbent natural or synthetic materials.

Figure 5:
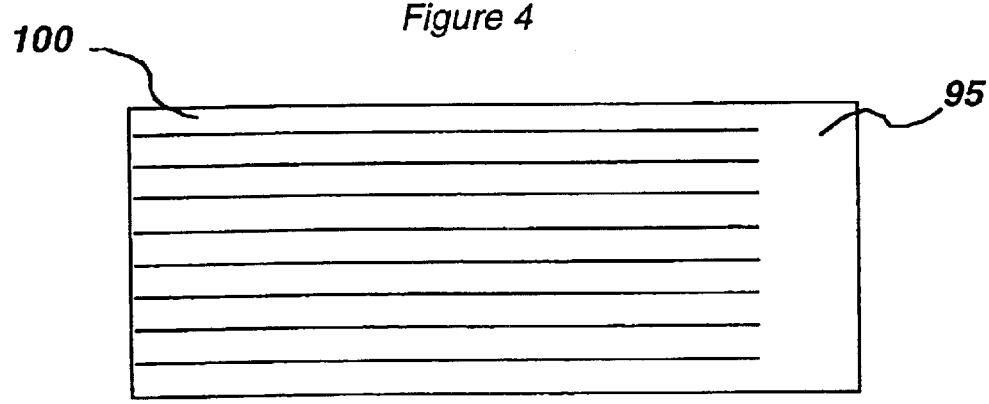
Figure 6:
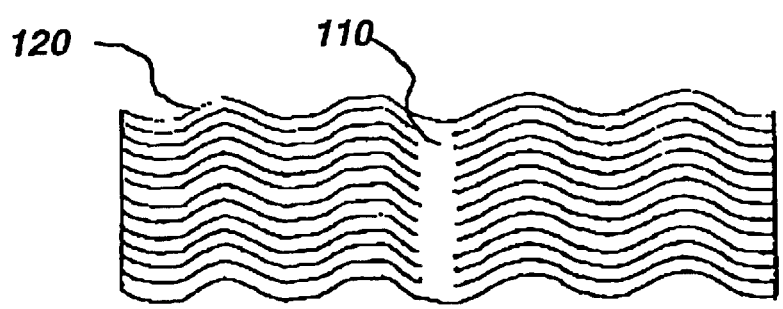
Figure 7:
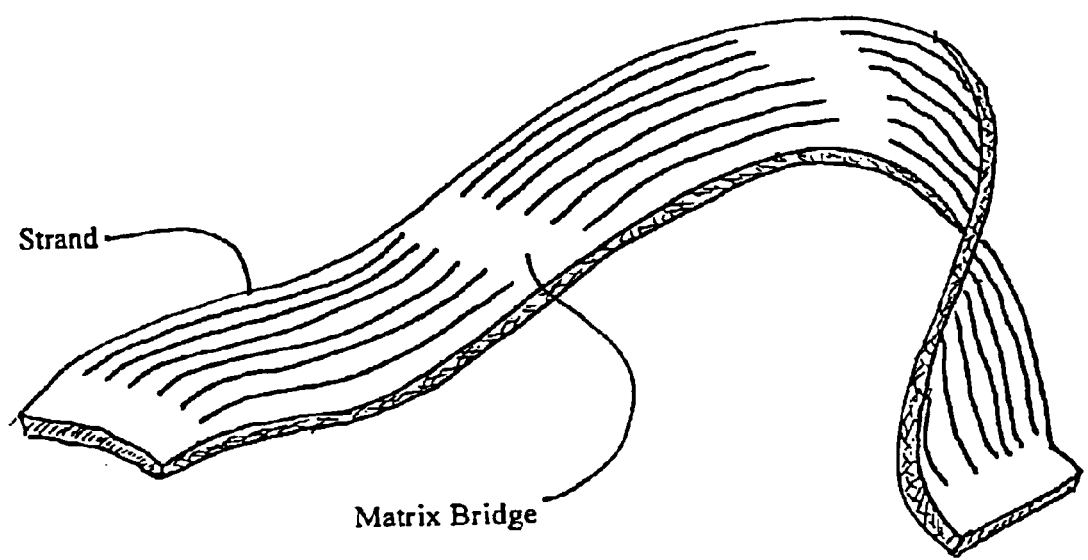

FIG. 4 illustrates a pattern that is an alternative embodiment. It is a circular pattern for making an embodiment 80 whereby the strands 90 radiate away from a central region of uncut matrix that joins the adjacent strands in the unit. FIG. 5 illustrates a pattern for making an embodiment whereby the bridge 95 of matrix is offset to one end of the pattern enabling the strands 100 to radiate away from the bridge in a single direction. FIG. 6 illustrates a pattern for making an embodiment whereby the strands 120 are irregular in shape over their length from the matrix bridge 100. FIG. 7 illustrates a pattern for making an embodiment whereby the strands are conjoined at several bridges along the length of the device and at the ends of the device. It is to be understood that the pattern can be any variation of these embodiments and is still within the scope of the present invention.

The unique stranded embodiment is particularly desirable because it enables the device to maintain its integrity and also maximize the surface area to volume ratio of its matrix. This is important since the matrix may be an absorbent material where a high surface area to volume ratio increases the rate of absorption, without increasing the overall absorption capacity of the device.

In a preferred embodiment, the wound dressing is principally constructed of a "stranded" matrix, which allows for optimal contact between the strands and the wound area. In addition, the stranded matrix construction maximizes the overall flexibility and pliability of the dressing. In embodiments of the device where multiple strands are employed, the overall flexibility and conformational characteristics of the device are maintained by binding strands in only limited and restricted areas. Minimal binding of the strands prevents the formation of rigid areas and allows for the effective and optimal utilization of numerous strands in a single device without adversely diminishing contact with the surface of the wound bed.

Preferred embodiments of the present invention comprise stranded matrices with antimicrobial activity. Preferably, the embodiments comprise antimicrobial activity provided by the methods of silver incorporation into the matrix.

Another advantage of the stranded matrix construction is the "semi-porous" quality of the wound dressing that allows for the removal of extraneous cellular matter resulting during the wound healing process. The air in the inter-strands area of the device serve as a reservoir of space that may be displaced allowing for the removal of excess materials such as exudate fluid, debridement product and cellular exudate from the wound bed. As this region fills, the device may swell to provide "support" to the wound bed and surrounding tissues. A wound constitutes damaged or "missing" tissue, and when tissue is missing, the surrounding tissue may "collapse" or sag into the void. "Support" in this context therefore, means the temporary filling of the void to hold the surrounding tissue in place where it should reside.

Removal of debridement product and cellular exudate is further facilitated by unbound, loose strands of the wound dressing devices. When placed upon a wound, the loose strands of the devices randomly orient in the wound bed where the thin filamentous strands and free floating ends contribute to mechanical debridement of necrotic slough. Since the strands are secured and bound in at least one region, a mechanical union is formed, ensuring that all strands and necrotic tissue accumulation in the inter-strand spaces are removed from the wound when the device is changed. By contributing to the removal of extraneous wound products and cellular debris, the wound dressing device permits cleaning of the wound which in turn prevents and decreases the possibility of infection and contamination.

In one embodiment, the wound dressing device is constructed from a matrix composed of an absorbent synthetic polyacrylate material. The rate of absorption of polyacrylate is significantly increased by cutting the material into strands, which increases the surface area to volume ratio. Polyacrylate material is particularly suitable for the wound dressings of the present invention because it retains its integrity during interaction with wound exudate moisture, as well as with necrotic tissue and wound debris. The wound dressing device of the present invention does not dissolve, gel or otherwise disintegrate during application to the wound. The preferred matrix swells slightly during the absorption of moisture, causing the device to conform closely to the walls of the wound bed.

In a preferred embodiment, the polyacrylate matrix is cut into free-floating strands bound together through a matrix-bridge in the mid-region. This pattern of construction imparts a significantly high surface area to volume ratio for rapid moisture movement within the absorbent matrix.

Wound dressing devices of the present invention may be produced by cutting a desired design pattern from stock sheets of matrix material. For example, the material may be die-cut from stock sheets of an absorbent polyacrylate wound dressing material. The stranded cut-out may then be coated with an agent to prevent aggregation and tangling of the free floating strands. Coating agents that may be used include, but are not limited to, petrolatum, talcum, polyglycols, glycerol, propylene, glycol, vegetable oil, and animal oil. Following the steps of cutting and coating, the material may be sterilized using sterilization techniques known in the art such as gamma radiation, steam and heat sterilization, electron beam or chemical sterilization (such as by use of ethylene oxide).

A preferred composition of the present invention comprises a matrix comprising a scaffolding polymer, a non-gellable polysaccharide, and one or more active agents incorporated therein. A more preferred matrix comprises an acrylamide polymer, guar gum, and one or more active agents incorporated therein. A most preferred matrix comprises an acrylamide polymer, guar gum, has one or more active agents incorporated therein, and is formed into a stranded structure wherein the strands are secured by at least one common region.

The wound dressing devices of the present invention may be used on injured tissue and for bodily fluid drainages where control and management of fluid and secretions is desired. The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions.

In particular, the wound dressing devices of the preferred embodiments are especially applicable for usage on heavily exudating acute and chronic wounds for controlling accumulating exudate moisture, support of the wound bed and surrounding tissues. Importantly, the wound dressings are particularly effective for stimulating and supporting autolytic debridement, and therefore accelerating the wound healing process.

In use, the wound dressing devices of the present invention are the primary dressing placed in direct contact with the wound bed, or as near as practical against the wound bed. The devices may serve as a packing material and, if required, may be secured into position with any suitable secondary wound dressing such as a wrap, tape, gauze, or pad. The dressings are temporary, however, and are not intended for permanent incorporation into the healed tissues. When necessary, the wound dressing devices are changed by first removing any over-dressing material and then removing the device, whereby any accumulated necrotic tissue and exudate is lifted away. The wound dressing devices of the present invention may be replaced by a fresh device or other suitable wound covering.

The devices may be placed in their entirety into a wound, placed in combination with additional bundles of the same design into the wound, or cut through the bridge between strands to reduce the size or number of strands present in the wound.

The devices of the present invention may be cut, shaped and modified to accommodate numerous uses and applications. For example, the devices may be used as a gastric retrievable device, wherein a retrieval cord is attached to the device that is then swallowed. After absorption has taken place, the devices may be retrieved and analyzed for content.

The devices may undergo a swelling action as they absorbs exudate moisture, however, they will not dissolve or disintegrate. The swelling action displaces necrotic material from the wound surface and forces the material into the inter-strands regions of the device. The laden moisture content and the retention of moisture near the wound bed by the invention contributes to stimulation of the autolytic debridement process whereby the body's own enzymes break-up necrotic tissue and cellular debris. Complete removal of the device occurs due to the conjoined nature of the device.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Formation of a Matrix Including Acrylamide

A mixing tank was charged with 161.4 kg of water and 9.1894 kg of acrylamide, 0.10347 kg of NNNN'-methylenebisacrylamide, and 9.3046 kg of glycerol were added and mixed. Then 1.0213 kg of guar gum non-gellable polysaccharide was dispersed in a mixture containing 0.9770 kg of isopropyl alcohol and 2 kg of water. The solution of guar gum was then added and dispersed into the acrylamide mixture. After suitable mixing, 0.1042 kg of TEMED was added and polymerization was catalyzed with 0.0999 kg ammonium persulphate.

While the batch was still liquid, it was poured into molds to form sheets. After gelling had occurred, sheets were transferred to a dessicator and dehydrated to form a stable intermediate stock sheet. Prior to cutting to size, the stock material was re-hydrated in a humid atmosphere. After cutting, the material was coated with petrolatum. The resulting wound dressing device was then sealed into appropriate packaging and irradiated to sterilize it.

EXAMPLE 2

Absorption Capacity of Polyacrylamide Matrix

It was determined that a preferred matrix material composed of cross-linked polyacrylamide and embedded natural vegetable gum absorbed approximately seven times its weight in water. Saturation of a flat sheet of matrix material with a thickness of 0.9 mm was achieved in approximately 22 hours of continuous exposure to excess water. A similarly sized piece of flat matrix material was cut into thin strands with a calculated 200% increase in overall surface area. The total water absorption of this material was also approximately seven times its weight. However this material achieved saturation in approximately five hours. Similar comparisons were made between an intact matrix and a matrix cut in such a way as to increase the surface area between 150% and 300%. These studies revealed that the matrices retained their overall absorption capacity but there was an increased rate of absorption proportional to the increase in surface area.

EXAMPLE 3

Matrix Absorption Capacities for Various Natural Substances

Matrices, cut into strands, were tested for absorption capacities on a variety of natural aqueous based viscous fluids. These fluids included water containing salt (0.15 M salinity), cow's whole milk, egg whites from chicken eggs, yogurt, and fetal bovine serum. The absorption of moisture by the test matrix strands ranged between 3.2 and 7.3 times the original weight of the tested devices.

EXAMPLE 4

Absorption Capacity of Matrix in Heterogeneous Biological Fluid

A polyacrylamide matrix of a preferred device was placed into a test tube containing fetal bovine serum, in an amount equal to five times the weight of the matrix. The matrix absorbed the aqueous fluid from the serum, leaving a concentrate of serum proteins in approximately four hours at 4° C. The concentrated serum proteins were predominately located between the strands of the device as a thick viscous coagulation. When the device was removed from the tube, the concentrated proteins were also removed. This experiment showed that the design would assist in the debridement of the wound.

EXAMPLE 5

Construction of Stranded Matrices

Initial prototypes of the stranded matrices were prepared by taking flat sheets of polyacrylamide matrix and cutting them into thin strands using a sharp instrument such as a box knife. Several methods were tested to determine a satisfactory method for commercial production of the device. The following tests were carried out with success:

Test 5(a). Matrix material was processed through a pasta cutter using a blade for noodles.

Test 5(b). A steel rule die was constructed such that parallel bands of steel rules, separated by spacers were locked into a die block. Matrix was cut by placing the die over the matrix and press-cutting with a hydraulic press.

Test 5(c). Matrix formula was compounded and catalyzed to initiate polymerization. The matrix was then placed into a 50 ml syringe and extruded as a thin strand onto a sheet. The thin strands were allowed to complete polymerization and then were dried and cut to uniform lengths for use in the device.

Test 5(d). A rotary die was constructed with a preferred pattern. The rotary die was placed into the rotary die assembly and matrix was fed through between the rotary die and the anvil for cutting.

EXAMPLE 6

Optimization of Matrix Construction Utility

Several prototypes were constructed to optimize the utility of the device as follows:

Test 6(a) Individual strands cut from a sheet of matrix were banded together using a silicone elastomer ring. The ring, having an internal diameter of approximately 3 mm and a length of 1.5 mm, was stretched open so that between five to seven strands could be threaded through and secured by the band about the middle. When placed into fluid for absorption studies, it was found that the unit nature of the device was retained throughout the absorption period and that the whole device was removed without leaving remnants in the absorption chamber.

Test 6(b) Prototypes constructed by using one strand to tie other strands together performed satisfactorily in absorption and retrieval studies.

Test 6(c) Prototypes constructed by maintaining a continuous bridge of matrix between adjacent strands were tested and shown to perform satisfactorily in absorption and retrieval studies.

EXAMPLE 7

Incorporation of Penicillin G into the Matrix

The incorporation of the antimicrobial agent, penicillin G, into the matrix was evaluated by dissolving $1\times10^6$ units of penicillin G powder into 50 milliliters of water. Acrylamide, methylenebisacrylamide, glycerol, and a guar gum/ isopropyl alcohol mixture were added to a flask containing 900 ml water and mixed for two hours. The penicillin solution was then added to the flask along with TEMED dissolved in 25 ml water. After thorough mixing, ammonium persulphate in 25 ml water was added and mixed thoroughly. The mixture was then poured into sheet molds and allowed to gel. The sheets of semi-solid gel material were stripped from the mold and dehydrated to approximately 7% their original water content for storage. Prior to testing, the sheets were placed in a humidified environment until the sheet weight had increased to approximately 118–122% the storage weight. Discs of 0.7 cm diameter were cut from the sheets. The discs were placed onto the surfaces of agar plates that had previously been seeded with various strains of microorganisms (Staph aureus; E. coli; Candida albicans; Ps aeruginosa). The plates were incubated and then examined for zones of inhibition around the discs containing antibiotic verses control discs. Zones of inhibition were measured around the penicillin containing matrix but not the control matrix on the Staph aureas, E coli, and Pseudoinonas aeruginosa plates. No zone was measured on the Candida albicans plate. These results demonstrate the release of active penicillin G after its incorporation into the matrix.

EXAMPLE 8

Incorporation of Silver Chloride Precipitate into the Matrix

Silver chloride is a weakly soluble salt that dissociates in water to release the silver ion that may have antimicrobial activity. Silver nitrate was dissolved into the batch mixture of pre-polymerized matrix at a concentration of $5 \times 10^{-3}$ M and then mixed well. The silver was precipitated by the addition of sodium chloride to produce a colloidal suspension of the weakly soluble salt. The batch was then polymerized by the addition of TEMED and ammonium persulphate and cast into sheets. The sheets were dehydrated to approximately 5% of the original moisture content and stored in the dark. Before testing, the sheet stock was hydrated to 118–122% its storage weight and then cut into 0.7 cm discs that were placed on the surface of pre-inoculated agar culture plates. The plates were incubated and then evaluated for growth around the discs.

Zones of inhibition were measured around discs on plates inoculated with Staph aureus; E. coli; Candida albicans; Pseudomonas aeruginosa, indicating the release of active silver ions after incorporation into the matrix. Hydrated sheets exposed to continuous light turned from an amber color to a uniform tan to brown color which illustrated uniform dispersion of the silver chloride precipitate. This also showed the susceptibility of the product to discoloration due to exposure to light when a stabilizing solution such as that of copper or ferric ions, was not added to the mixture.

EXAMPLE 9

Synergistic Action Between Therapeutic Agent and Adjuvant

The antifungal agent Zn-pyrithione is an active agent against a wide range of pathogenic fungi but it poorly penetrates heavily keratinized tissues such as finger and toe nails. Matrix material containing Zn-pyrithione and the keratinolytic agents salicylic acid and urea were tested for increased efficacy of delivering agents to control fungal growth in nail tissue. To the pre-polymerized batch material was added sufficient Zn-pyrithione, salicylic acid and urea to give final concentrations of 0.01%, 5% and 5%, respectively. The batch was neutralized to pH 6.5 by the addition of sodium hydroxide. After thorough mixing, the batch was poured into molds to cast into sheets. After gelling, the sheets were dehydrated to 5% the original moisture content and stored. Before testing, the sheet stock was hydrated to 118–122% its storage weight and then cut into 0.7 cm discs which were placed on the surface of bovine hoof material cut thinly to resemble finger nail. These were then transferred onto pre-inoculated agar culture plates. The plates were incubated and evaluated for growth around the discs.

Zones of inhibition were measured around the discs on plates inoculated with Canidida albicanis. No zones were measured where Zn-pyrithione or the keratinolytic agents were not included in the matrix. Smaller zones were measured where only urea and Zn-pyrithione were added. Zones of inhibition were however measured around sets that contained both the active agent and the keratinolytic agents in combination. These results demonstrate that therapeutic agents and adjuvants may be incorporated into the matrix and later released in active form such that they work synergistically.

EXAMPLE 10

Bovine Protein Incorporation into and Delivery from the Matrix

Bovine serum albumin (approximately 65,000 Daltons) and bovine gamma globulin (approximately 155,000 Daltons) were dissolved at a concentration of 0.1% w/w into a pre-polymerized matrix batch material and thoroughly mixed. The batch was polymerized by the addition of TEMED and ammonium persulphate, poured into molds and gelled into sheets. The sheets were dehydrated to approximately 5% the original moisture content and stored. Before testing, the sheet stock was hydrated to 118–122% its storage weight and then cut into 0.7 cm discs which were placed on the surface of saline agar plates. The plates were incubated for 24 hours at 4° C. and then developed by the addition of 0.25 M HCl solution which causes proteins to precipitate. Zones of protein precipitate were measured only around the discs that had protein incorporated into the matrix, indicating the release of active protein after its incorporation into the matrix.

EXAMPLE 11

Interleukin-2 Incorporation into and Delivery from the Matrix

The growth factor interleukin-2 was incorporated into polymerized matrix material by soaking re-hydrated plain stock sheet in fluid containing the growth factor. After 24 hours of soaking at 4° C., the matrix pieces were cut into one cm circles and placed into saline. Samples of the elution fluid were taken at intervals and assayed by ELISA (Enzyme Linked Immunosorbent Assay) for interleukin-2 to determine if material entered the matrix and was then released. The results showed that proportionately more IL-2 was eluted from the matrix over time.

EXAMPLE 12

Temporal Release of Antifungal Agent

Fluconazole was incorporated by the addition of the active agent to a pre-polymerized batch of matrix. After polymerization, dehydration and rehydration, a disc containing the active agent was placed onto an agar plate for two hours at 4° C. Thereafter, every two hours for a total of 154 hours, the disc was removed and transferred to a new spot on the surface of the agar. After all transfers had been carried out, the plates were inoculated with Candida albicatis and incubated at 35° C. until confluent growth had occurred. The serial transfer spots on the plates were then examined for zones of inhibition. The results showed that the device delivered a high dose of fluconazole in the first eight hours and then a steady concentration thereafter until the 140th hour when the concentration, according to zone size, began to diminish.

EXAMPLE 13

Delivery of a Biologically Functional Protein from the Matrix

Human transferrin is an iron chelating protein of approximately 70,000 MW. Transferrin was incorporated into the pre-polymerized batch mix at 0.05% w/w, mixed, and then encapsulated by polymerization with TEMED and ammonium persulphate. After dehydration, rehydration and cutting, discs of 0.7 cm were placed onto the surface of nutrient agar plates and incubated at 4° C. for 24 hours. The discs were then removed and the plates were inoculated with Staph aureus and then incubated at 37° C. overnight. The plates were examined for zones of inhibition where the transferrin removed the trace element iron from the nutrient. Human transferrin retained its biological activity during incorporation, processing and testing as measured by the zones of inhibition around the spots where transferrin-containing discs had been placed.

EXAMPLE 14

A wound healing device comprising a polyacrylate hydratable matrix produced according to U.S. Pat. No. 5,196,190 and containing silver was made using the following steps. The silver containing polyacrylate matrix was made by mixing 185 g acrylamide and 2 g bisacrylamide into 3330 g of water containing between 33.3 g of sodium chloride. To this mixture, was added 21 g of guar gum and 188 g of glycerol. After mixing to homogeneity, a solution containing 0.563 g silver nitrate was slowly added to the mixing batch. After formation of the finely dispersed silver complex, either from 0.16 g copper chloride ($CuCl_2$) or 0.46 g ferric chloride $FeCl_3$ was dissolved into the mixture The polymerization of the mixture was accomplished by blending 1.8 ml TEMED and 2.6 g ammonium persulphate into the mixture. The mixture was poured into the appropriate molds before polymerization in a dark place. The gelled polymer was removed from the mold, dehydrated by mild heat in a darkened drier and then rehydrated by humidification to a desired moisture content, 22% w/w. The matrix was then cut if necessary, packaged, and sterilized by irradiation of electron beam or gamma irradiation.

EXAMPLE 15

This Example shows the antimicrobial activity of the silver-containing matrix wound dressings of Example 14 in a zone inhibition assay. Fresh overnight suspension cultures of each of various medically important bacteria and fungi were coated onto the surface of trypticase soy agar, for bacteria, or Sabouraud's agar plates, for fungi. Circles 5 mm in diameter, were cut from the silver-containing dressings and from control dressings that do not contain silver. The circles were placed on the surface of the cultured plates which were then incubated for 24–48 hours. Zones of inhibition were measured at the completion of the incubation phase. The diameter of the zones were measured and are expressed in Table 1.

TABLE 1

| | Strain of organism | |
|---|---|---|
| | Zone of Inhibition (mm) | |
| Dressing | AcryDerm Silver | Control |
| Staph. aureus | 19 | <5 |
| Staph. aureus (coagulase -) | 28 | <5 |
| Staph. aureus (MRSA) | 16 | <5 |
| Group A Streptococcus | 23 | <5 |
| Bacillus subtilis (spore former) | 15 | <5 |
| Listeria monocytogenes | 18 | <5 |
| Ps. Aeruginosa | 21 | <5 |
| E. coli | 20 | <5 |
| Proteus mirabilis | 16 | <5 |
| Enterobacter faecalis | 20 | <5 |
| Enterobacter cloacae | 9 | <5 |
| Kleb. Pneumoniae | 20 | <5 |
| Candida albicans | 13 | <5 |
| Candida parapsilosis | 20 | <5 |
| T. rubrum | 15 | <5 |
| M. gypseum | 9 | <5 |

EXAMPLE 16

This example was directed to showing that the devices of the present invention, comprising a matrix with silver incorporated, such as those made by the methods of Example 14, was stable to light. This was done by preparing 1 inch circles of silver-containing matrix that were then stored in the dark. Each day for 7 days a 1 inch circle of matrix was transferred from dark to a lighted area so that at the end of the $7^{th}$ day a total of 8 circles had been exposed to light for between 0 time and 7 days.

Dressing circles that contained silver chloride without the photostablization chemistry were treated identically. The dressings that had no photostabilization chemistry had reacted by the formation of a blackening in the matrix. The blackening was proportional to the amount of time the matrix had been exposed to light. By contrast samples that were stabilized by either copper or iron did not show discoloriazation.

EXAMPLE 17

The sustained release of silver was shown in this example using the dressing made in Example 14. This was demonstrated by seeding agar nutrient plates with a test strain of microorganisms daily for 6 days. The trypticase soy agar were inoculated with a fresh overnight inoculum of Staph. aureus. The plates were then incubated for 24 h at 37° C. The zones of inhibition were then measured before transferring the dressing circles to a freshly inoculated plate of TSA. This process was repeated daily for 5 days to measure the release of antimicrobial activity into the culture plate.

Figure 8:
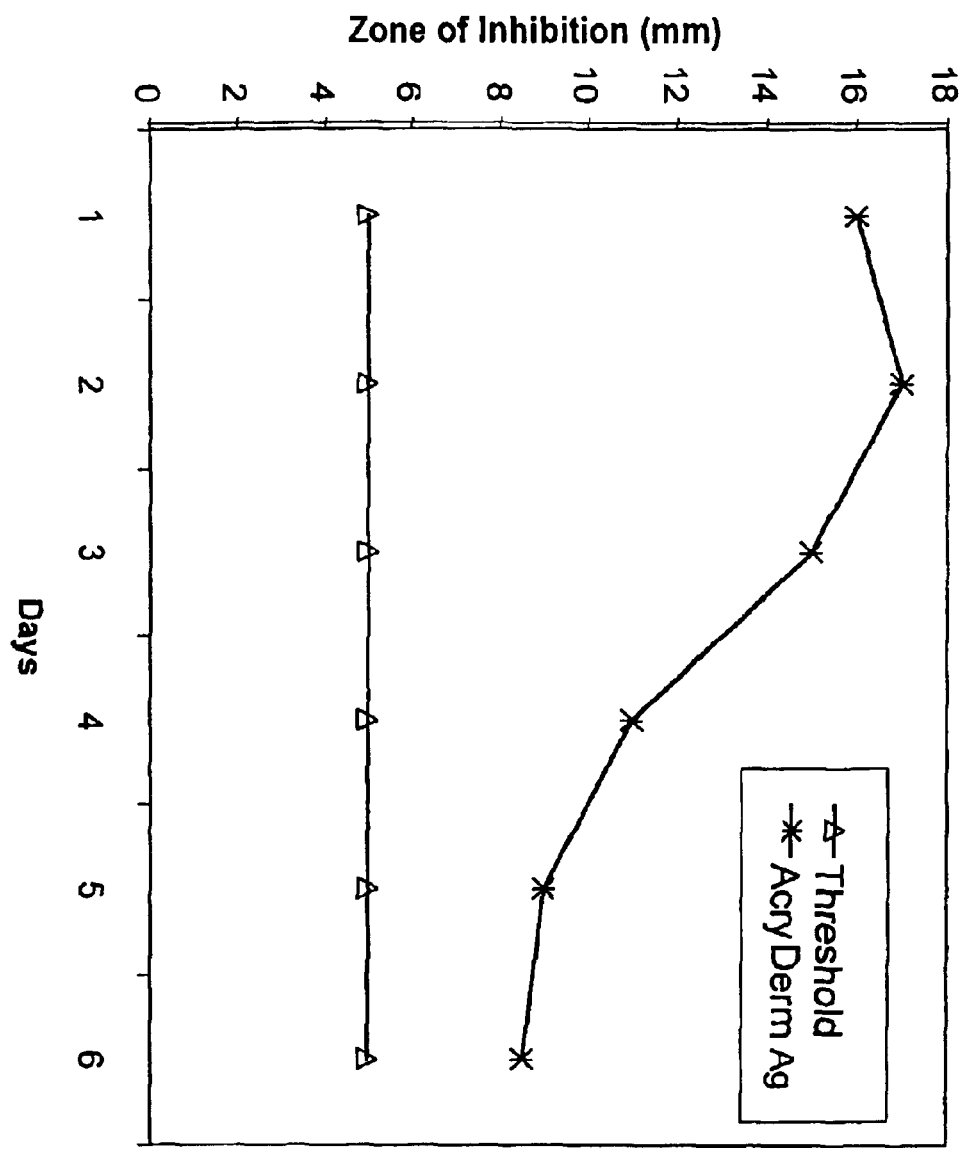
FIG. 8 shows a graph of the sustained release activity of a silver-containing matrix wound dressing.

To clarify, on day 1, a piece (5 mm circle) of silver-containing dressing was placed on the first plate and incubated for 24 hours. The circle was then transferred to the second plate for a further 24 hours and so on. Each plate was then incubated to determine the zone of inhibition around the area where the piece of matrix had been deposited. FIG. 8 shows the data of the silver-containing dressing and a control dressing that did not contain silver. The results showed that silver was released over a period of 6 days in a concentration sufficient to inhibit the growth of the indicator strain of bacteria used in the test.

EXAMPLE 18

Cytotoxicity of Silver-Containing Wound Dressings for Mammalian Cells

Figure 9:
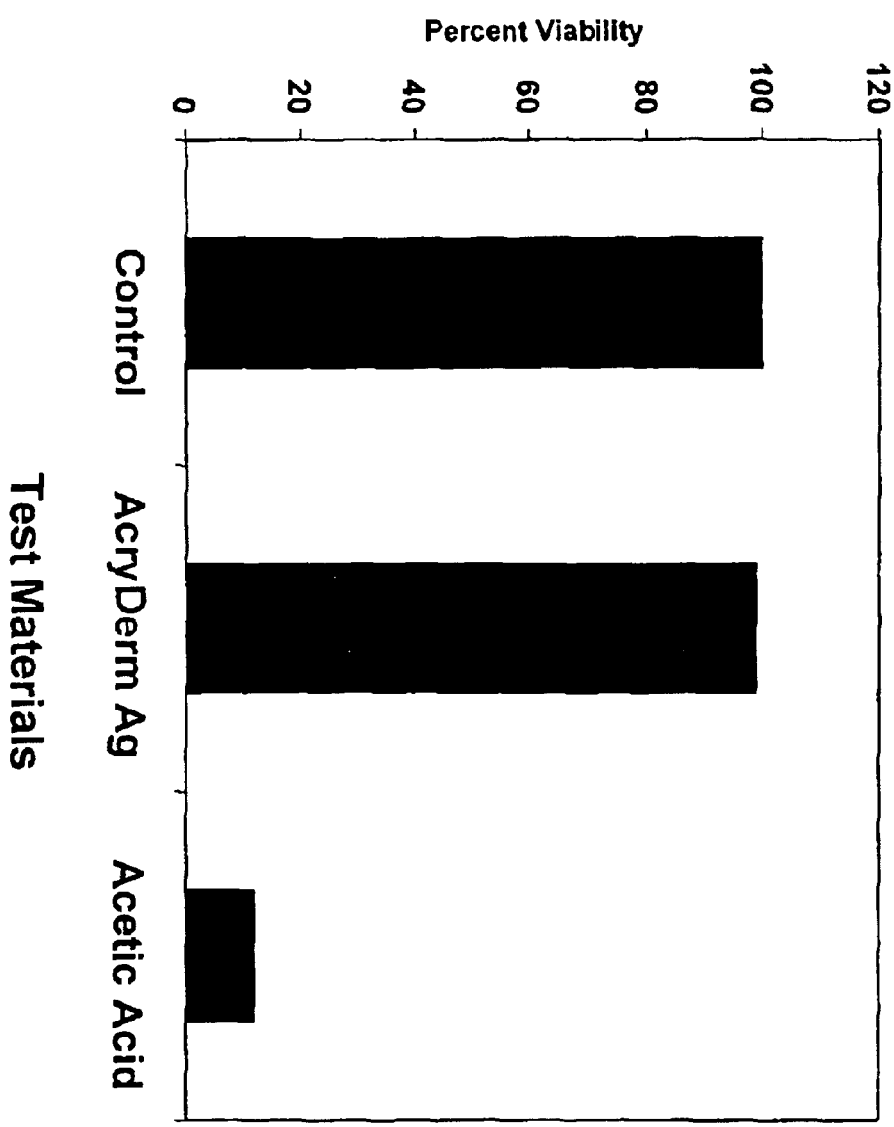
FIG. 9 shows a graph of the results of tests for cytotoxicity.

Tissue cytoxicity was evaluated by the in vitro method taught in the AAMI Guidelines for Biological Evaluation of Medical Devices. Samples of the silver-containing wound dressings of Example 14 were added to DMEM tissue culture medium and incubated. Fetal bovine serum was added before the samples were transferred to confluent monolayers of L-929 fibroblasts. The cultures were incubated at 37° C. in 5% $CO_2$ for 24 h. Alamar Blue vital dye was added for the last 4 h of incubation. The culture supernatants were removed, assayed for OD difference at 570 and 600 nm wavelength along with the positive (fresh medium alone) and negative (3% w/v acetic acid in saline) controls. The viability of fibroblasts was also evaluated by parallel cultures stained with the vital dye, trypan Blue (data not shown). The silver-containing dressing was indistinguishable from the positive growth control sample with greater than 99% of fibrobalsts over the culture period. The acetic acid solution caused a greater than 88% decrease in viability in the fibroblasts culture. These findings are consistent with microscopic observation of cultures treated with trypan blue vital dye (data not shown). FIG. 9 shows the results of the silver-containing dressing and the positive and negative controls.

EXAMPLE 19

Figure 10:
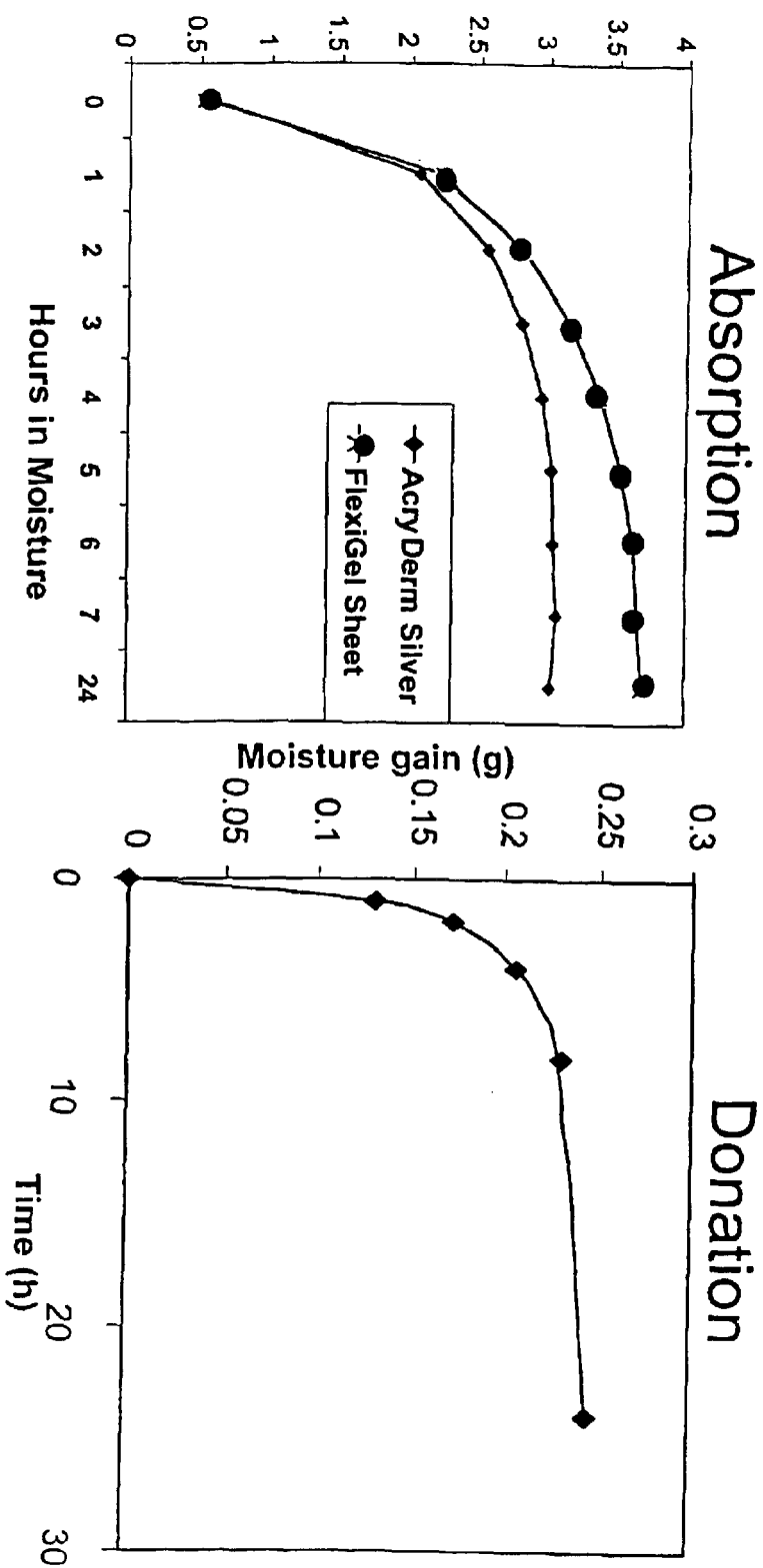
FIG. 10 shows graphs of the absorbency and moisture-donating ability of a preferred embodiment of the present invention.

This Example shows the absorbency profile of the silver-containing dressings of the present invention, such as that made by Example 14. Squares (2.5 cm) were cut from the matrix of Example 14 that does not contain silver, and the silver-containing dressing. These were weighed and then placed into isotonic saline solution at room temperature. At various intervals, each matrix was removed, damped of excess moisture and reweighed This procedure was repeated over the course of 24 h The hydrophilic base polymer alone increased by 720% in saline. The addition of silver to the matrix only slightly reduced its absorbency (605% vs 720%). FIG. 10 shows the absorption profile and the donation of moisture by the silver-containing dressing.

Donation of moisture testing was carried out by weighing the silver polyacrylate material onto dried pre-weighed filter paper and allowing it to stand for various intervals before re-weighing to detect moisture donation.

EXAMPLE 20

This Example was directed to showing the light stability and skin staining characteristics of silver-containing wound care dressings. Ionic silver (Ag+) is reduced to a black precipitate (Ag°) by light energy. The silver-containing matrix of Example 14 suppressed the light reaction of silver. This was demonstrated by exposing 2.5 cm circular samples of silver-containing matrix to light for various numbers of days. There was almost no darkening of the silver-containing dressing for up to 8 days of exposure to room light. By contrast, silver nitrate impregnated filter papers showed significant darkening within 24 h exposure to light.

When placed on skin and exposed to light, similar results were seen. The silver impregnated paper stained the skin whereas the silver-containing matrix did not.

EXAMPLE 21

Rate of Bacterial Killing

Figure 11:
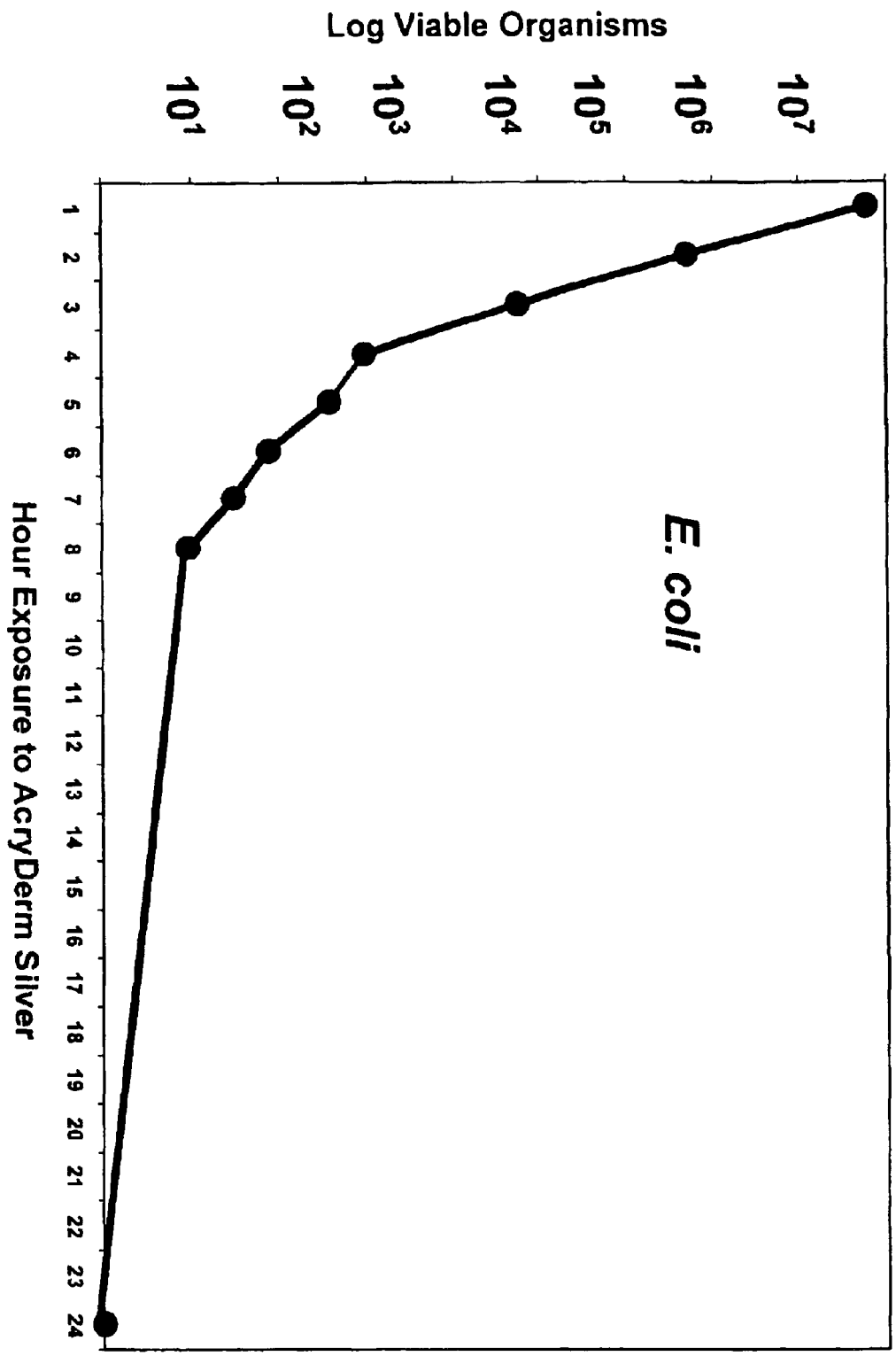
FIG. 11 shows the effect of a silver-containing device on the viability of an *E. coli* culture.

The time between exposure to the antimicrobial and the bactericidal event is related to the rate of release of silver from the matrix. The rate of killing of *E. coli* by silver-containing matrix from Example 14 was determined by suspending a 1 gram sample of matrix in a bacterial suspension. After various time intervals samples were removed and plated counted to determine the number of surviving bacteria. FIG. 11 is a plot of the number of surviving organisms at the various sample intervals following exposure to the silver-containing matrix.

EXAMPLE 22

Skin Bioburden

Continued silver ion formation and release from the silver containing polyacrylate is dependent upon disruption of the equilibrium between colloid and free ions in the aqueous phase of the matrix. Theoretically even small amounts of aqueous fluid added to the matrix will cause additional release of silver. Furthermore this released silver should be sufficient to be bactericidal to organisms in contact with the dressing.

This was illustrated by placing either silver-containing matrix of Example 14 or non-silver containing matrix on skin for a set time interval and then sampling under each of the matrices for surviving bacteria. Samples of matrix from example 14 along with plain non-silver containing matrix was placed on adjacent areas of the forearms of volunteers. 24 h later the specimens were removed and the areas in a precise 30 mm circle were swabbed and plated and counted to determine the microbial bioburden. The plain matrix served as the control for each of the five individuals. In all cases the presence of silver significantly decreased the bioburden compared to the plain matrix (see FIG. 12). Each line is the test of one individual.

EXAMPLE 23

Biocompatability Testing

Devices containing bioactive ingredients must be compatible with tissues to have utility in clinical applications. This is generally determined by testing the devices for their propensity to cause irritation or to induce sensitization. Skin irritation testing was carried out by securing 30 mm diameter pieces of the matrix of Example 14 to the forearms of volunteers for 7 days. Plain matrix without silver (FlexiGel) served as the known non-irritating control. Latex served as a probable irritating material. Specimens were secured by a polyurethane thin film adhesive dressing. At the conclusion of the induction phase the materials were removed and the areas were scored for erythema and induration consistent with irritation (see results in the table 2).

Sensitization is the induction of an immunological response to agents or sensitizers in the material. This was measured by the local lymph node assay which is carried out by placing test materials on the ears of nice each day for 5 consecutive days. On the fifth day the animals received a dose of radioactive thymidine for a pulse period of 4 hours. Thereafter the local draining lymph nodes were removed from the animals and measured for thymidine incorporation. The higher the level of incorporation the more sensitized the animals. The findings laid out in table 2 showed that none of the animals were sensitized to the silver-containing matrix of Example 14.

TABLE 2

Biocompatibility Testing

| Material Tested | Skin Irritation | Sensitization |
|---|---|---|
| FlexiGel | 0/5 | 0/5 |
|  | 0/6 | 0/6 |
| Silver-Containing Matrix | 0/5 | 0/5 |
|  | 0/6 | 0/6 |
| Medical Grade Adhesive | 1/5 | 0/5 |
| Latex | 2/6 | 0/6 |

EXAMPLE 24

AgCl Colloid Nucleation in Solvent for Aquacel

Example 24 was directed to the development of methods for the nucleation of. silver chloride in Aquacel (carboxymethoylcellulose, CMC) using water in IPA (Isopropyl alcohol) or EtOH (ethanol) as the delivery and permeation vehicles. One aspect of this Example was to establish solvent to water ratios for the precipitation of silver chloride into pre-formed filamentous materials such as Aquacel (CMC) and alginates.

Aquacel and alginates are hydrophilic materials that aggressively absorb aqueous solutions which often cause gelling of the matrix materials. Gelled materials may be subsequently dehydrated, but seldom retain their original properties after absorption of water. Therefore it is impractical to use a substantially aqueous vehicle for the delivery of ionic silver and chloride into the matrix material where nucleation in situ of colloid would be expected to occur. This excludes the method of precipitating AgCl in situ using water as solvent. Aquacel and alginates do not absorb alcohol, therefore a AgCl precipitation in a water;alcohol solution to partially hydrate fibers with reagents can be done.

A. This experiment of the Example showed the use of either acetone, isopropyl alcohol or ethanol as the solvent phase of an a substantially non-aqueous solution, also referred to herein as an aqueous:alcohol solution such as in an aqueous:alcohol bath for impregnation of silver into cross-linked carboxymethyl cellulose.

The following combinations of reagents were produced and tested for efficacy in allowing nucleation of AgCl in the solvent phase.
1) Add 0.177 g NaCl to 3.333 mL $H_2O$.
2) Add 90 g Acetone, IPA, or EtOH.
Add 6.666 mL $AgNO_3$ sol (0.11325 g/50 ml $H_2O$)
Observe precipitate formations

| Solvent | NaCl Addition | $AgNO_3$ Addition |
|---|---|---|
| Acetone | Precipitate formed | NA |
| IPA | Precipitate formed | ++Precipitate formed |
| EtOH | No precipitate | Fine precipitate |

It was concluded that the ethanol was the preferred alcohol for the delivery vehicle.

B. This experiment was carried out to determine if separate aqueous:alcohol solutions could be pre-made and then combined before the immersion of hydrophilic materials as an appropriate single bath method for impregnating hydrophilic polymers. Separate reagents were prepared according to the formula below and then combined together.
1) Add 0.221 g $AgNO_3$ to 200 μL $H_2O$ to 25 g EtOH
2) Add 0.5 g NaCl to 2 mL water to 25 g EtOH
Combine Solutions
Results: Immediately following combining of the reagents a heavy rapidly forming precipitate developed in the mixture. It was not appropriate to pre-mix separate solutions that are later combine to form the bath for the immersion of hydrophilic matrix material for impregnating with silver.

C. The purpose of this experiment was to determine if sodium thiosulfate dissolution of silver chloride would aid in the deposition of the antimicrobial silver in hydrophilic fibers. The reagents were prepared in the following fashion an observed for the formation of a fine precipitate after combination with either alcohol or water.
1) Add 0.177 g NaCl to 4 ml $H_2O$
2) Add 6 ml $AgNO_3$ sol (0.11325 g/50 ml $H_2O$)
3) Add 0.015 g Na thiosulfate to dissolve AgCl
4) Add half to 90 ml $H_2O$, half to 90 ml EtOH
The test showed that the addition of the reagent with sodium thiosulfate with ethanol allowed the formation of a precipitate but none formed when the reagent was added to water.

| Solvent | +AgCl (sol) |
|---|---|
| 90 mL $H_2O$ | no precipitate |
| 90 mL EtOH | preferred precipitate |

Sodium thiosulfate may interfere with nucleation of silver chloride in hydrophilic fibers.

D. The nucleation of silver chloride colloid in the hydrophilic polymer was accomplished by preparing an aqueous-:alcohol solution of sodium chloride in which various hydrophilic materials were immersed. After an appropriate time an aqueous:alcohol solution containing silver nitrate was added. The materials were then removed, blotted of excess materials and air dried. They were then tested for antimicrobial activity against *Staph. aureus* by zone inhibition assay, for skin staining properties and for discoloration in light.
1) Add 0.1777 g NaCl to 2 ml $H_2O$
2) Add 0.006795 g $AgNO_3$ to 100 μl $H_2O$
3) Add 25 g EtOH to NaCl and $AgNO_3$ solutions
4) Place a 2×2 in. square of Tegagen, Algisite M, Aquacel, or Algisite Rope into the NaCl solutions.
5) After a few seconds, add the $AgNO_3$ solution.
6) After a few seconds, remove dressings and blot dry.
7) Test for sustained release on staph zone inhibition plates, for skin staining, expose to light.

Antimicrobial Zone inhibition assay against *Staph aureus* in evaluation of sustained release over 3 days.
Serial Transfer of Antimicrobial Activity

| Dressing | Zone Inhibition to material size | | |
|---|---|---|---|
|  | Day 1 | Day 2 | Day 3 |
| Ag Tegagen | 10/5 | 8/5 | 8/5 |
| Ag Algisite M | 10/5 | 8/5 | 8/5 |
| Ag Aquacel | 10/5 | 8/5 | 8/5 |

-continued

| Dressing | Zone Inhibition to material size | | |
|---|---|---|---|
| | Day 1 | Day 2 | Day 3 |
| Ag Algisite Rope | 13/10 | 10/8 | 9/6 |
| Silver dressing | 12/8.5 | 10/8 | 10/9.5 |
| Aquacel C | 0 | 0 | 0 |

Skin staining caused by the topical application of the materials to intact skin and then observing for the occurrence of darkening around the application sites:

| Dressing Materials | |
|---|---|
| | Skin staining |
| Acticoat | yes |
| Ag-Aquacel | no |
| Acticoat wet | yes |
| Ag-Aquacel wet | no |

The light stability of the materials were evaluated after impregnation with silver either as dry substrate or after wetting with water.

| Dressing | Dry | Wet |
|---|---|---|
| Ag Aquacel | White, good, eventually purplish | Brown |
| Hi Ag-Aquacel* | Purple, specks | Dark gray |
| Aquacel C | White | Clear |

*This embodiment contains twice the amount of silver as the Ag Aquacel.

Overall Summary

Silver was incorporated into hydrophilic fibers in amounts that allowed for sustained release. IPA or acetone may be used with more soluble chloride salts ($CuCl_2$, $FeCl_3$) but ethanol is the preferred solvent when using sodium chloride. The resulting materials possess antimicrobial activity and do not appreciably discolor in the presence of light.

EXAMPLE 25

Titration of the NaCl, Ag, Cu Concentrations for Effecting Impregnation of Stabilized Silver into Aquacel This Example was designed to develop a method for incorporating AgCl into Aquacel fibers to form a color stable, sustained release antimicrobial hydrophilic material for wound care applications.

It is possible to add AgCl to fibers so that it may be released over a sustained period of time. Sustained release characteristics are imparted by the size and location of nucleated silver chloride in the hydrophilic fibers. The stability of the material to light is controlled by the amount of NaCl, and the location and concentration of Cu ions in the material.

The following ratios of reagents were prepared and used to impregnate 2×2 inch samples of carboxymethyl cellulose (Aquacel). The stock solution of silver used in these tests was 0.11325 g Ag/50 mL $H_2O$. The stock solution of copper ions was 0.0495 g Cu/10 g EtOH.

a. 0.1777 g NaCl in 2 ml $H_2O$, add to 50 g EtOH, add dressing, add 6 mL $AgNO_3$ sol., add 0 µl Cu
b. 0.1777 g NaCl in 2 ml $H_2O$, add to 50 g EtOH, add dressing, add 3 mL $AgNO_3$ sol., add 0 µl Cu
c. 0.1777 g NaCl in 2 ml $H_2O$, add to 50 g EtOH, add dressing, add 6 mL $AgNO_3$ sol., add 333 µl Cu
d. 0.1777 g NaCl in 2 ml $H_2O$, add to 50 g EtOH, add dressing, add 3 mL $AgNO_3$ sol., add 333 µl Cu
e. 0.0888 g NaCl in 2 ml $H_2O$, add to 50 g EtOH, add dressing, add 6 mL $AgNO_3$ sol., add 0 µl Cu
f. 0.0888 g NaCl in 2 ml $H_2O$, add to 50 g EtOH, add dressing, add 6 mL $AgNO_3$ sol., add 500 µl Cu
g. 0.0888 g NaCl in 2 ml $H_2O$, add to 50 g EtOH, add dressing, add 3 mL $AgNO_3$ sol., add 0 µl Cu
h. 0.0888 g NaCl in 2 ml $H_2O$, add to 50 g EtOH, add dressing, add 3 mL $AgNO_3$ sol., add 500 µl Cu
i. 0.01359 g $AgNO_3$ to 100 µl $H_2O$, add to 25 g EtOH/0.0888 g NaCl in 2 ml $H_2O$, add 0 µl Cu, add to 25 g EtOH, add dressing, add $AgNO_3$ solution.
j. 0.01359 g $AgNO_3$ to 100 µl $H_2O$, add to 25 g EtOH/0.0888 g NaCl in 2 ml $H_2O$, add 500 µl Cu, add to 25 g EtOH, add dressing, add $AgNO_3$ solution.
k. 0.006795 g $AgNO_3$ to 100 µl $H_2O$, add to 25 g EtOH/0.0888 g NaCl in 2 ml $H_2O$, add 0 µl Cu, add to 25 g EtOH, add dressing, add $AgNO3$ solution.
l. 0.006795 g $AgNO_3$ to 100 µl $H_2O$, add to 25 g EtOH/0.0888 g NaCl in 2 ml $H_2O$, add 500 µl Cu, add to 25 g EtOH, add dressing, add $AgNO_3$ solution.
m. 0.006795 g $AgNO_3$ to 100 µl $H_2O$, add to 25 g EtOH, add dressing/0.0888 NaCl in 2 ml $H_2O$, add 0 µl Cu, add to 25 g EtOH, add to $AgNO_3$ solution.
n. 0.006795 g $AgNO_3$ to 100 µl $H_2O$, add to 25 g EtOH, add dressing/0 NaCl in 2 ml $H_2O$, add 0 µl Cu, add to 25 g EtOH, add to $AgNO_3$ solution.
o. Add 10 g $H_2O$ to 25 g EtOH, add dressing Samples were immersed then removed from the bathes and blotted then dried in air. A portion of each sample was exposed to light as well as for antimicrobial activity against *Staph. aureus*.

Results

Samples that contained higher concentrations of silver discolored more quickly in light with most samples eventually turning a purplish color. The exceptions were samples "n" and "o" which remained white. With the exception of the sample developed from the combination in "o", the samples had an acceptable feel and texture. Sample "o" was stiff following processing. All samples produced the same size zone of inhibition on the staph plate except for sample "o", which had no zone of inhibition.

EXAMPLE 26

A Comparison of Silver Chloride Nucleation in Solutions Containing Both Silver and Chloride Ions vs. Separation of the Reagents Previous evaluations of the process incorporated the silver into a bath that contained the hydrophilic fibrous materials. This resulted in the formation of a desirable effect but had the disadvantage that solutions could not be re-used. This evaluation was undertaken to deterrnine if nucleation occurred when materials were first treated with chloride ion containing reagent then rinsed before immersion into a silver ion containing reagent bath.

Experimental Design: Specimens of carboxymethylcellulose were impregnated with silver by the following methods.

1) 2×2 inch specimen of Aquacel were impregnated with silver by:
Prepare an aqueous:ethanol solution by adding 0.0888 g NaCl in 2 ml $H_2O$ to 25 g EtOH. Place a 2×2 in sample of Aquacel into the solution for 20 seconds and then remove. Rinse in ethanol 3 times to remove excess chloride ions from the surface then place the sample in an aqueous:alcohol solution made by combining 0.006795 g $AgNO_3$ in 100 μl $H_2O$ to 25 g EtOH. Allow the specimen to stand for 10 seconds then remove, rinse and blot dry before testing for stability to light and for sustained release of antimicrobial activity.
Prepare an aqueous:ethanol solution by adding 0.0888 g NaCl in 2 ml $H_2O$ and 500 μl Cu solution (0.0495 g Cu/10 g EtOH) to 25 g EtOH. Place a 2×2 in sample of Aquacel into the solution for 20 seconds and then remove. Rinse in ethanol 3 times to remove excess chloride ions from the surface then place the sample in an aqueous:alcohol solution made by combining 0.006795 g $AgNO_3$ in 100 μl $H_2O$ to 25 g EtOH. Allow the specimen to stand for 10 seconds then remove, rinse and blot dry before testing for stability to light and for sustained release of antimicrobial activity.

Control samples were prepared by soaking specimens in aqueous:ethanol solutions made by adding 0.0888 g NaCl in 2 ml $H_2O$ with either 500 μl or 1000 μl Cu solution (0.0495 g Cu/10 g EtOH) to 25 g EtOH. After 10 seconds of soak the aqueous:alcohol solution was made by combining 0.006795 g $AgNO_3$ in 100 μl $H_2O$ to 25 g EtOH was added directly to the first mixture, allowed to stand for 20 seconds before removal, blotting and drying.

2) Blot to dry, expose to light and test for zones of inhibition with staph.

| | Zones of Inhibition (mm) Serial Transfer in days | | | | | | | | | |
|---|---|---|---|---|---|---|---|---|---|---|
| Sample | 1 | 2 | 3 | 4 | 5 | 6 | 7 | 8 | 9 | 10 |
| Control, low CU | 9.5 | 9 | 6.5/4 | 6/4 | 5/4 | 0 | 0 | 0 | 0 | 0 |
| Control, High Cu | 10 | 9 | 7/4 | 6/4 | 6/4 | 6/4 | 5/4 | 4.5/5 | 5.5/5 | 5.5/5 |
| Rinse w/o Cu | 6.5 | 5/4 | 0 | 0 | 0 | 0 | 0 | 0 | 0 | 0 |
| Rinse w/Cu | 7 | 5/4 | 0 | 0 | 0 | 0 | 0 | 0 | 0 | 0 |

The results showed that chasing in silver ions after chloride ion impregnation does lead to the development of antimicrobial activity. However the activity level was lower than that for materials developed by adding the silver ion to the chloride ion in the same batch

EXAMPLE 27

Impregnation of Various Hydrophilic and Non-Hydrophilic Materials with the Silver Impregnation Technology This Example was to determine whether the solvent precipitation method can be used on other fibrous materials.

Samples of a variety of materials were treated by the common bath impregnation methods to convert them into sustained release antimicrobial materials. The materials were prepared into 2×2 inch pads and included Kaltostat alginate pad, Curity gauze sponge, NuGauze, Telfa non-adherent pads, Kaltostat alginate rope, and Aquacel. The procedure for impregnation was carried out as described below. Where Cu was incorporated into the procedure it was drawn from a stock solution at 0.0495 g Cu/10 g EtOH.

Procedure

Samples were prepared by soaking specimens in aqueous:ethanol solutions made by adding 0.0888 g NaCl in 2 ml $H_2O$ with 500 μl Cu solution to 25 g EtOH. After 10 seconds of soak the aqueous:alcohol solution made by combining 0.006795 g $AgNO_3$ in 100 μl $H_2O$ to 25 g EtOH was added directly to the first mixture, allowed to stand for 20 seconds before removal, blotting and drying.

B. Samples were prepared by soaking specimens in aqueous solutions made by adding 0.0888 g NaCl in 2 ml $H_2O$ with 500 μl Cu solution to 25 g $H_2O$. After 10 seconds of soaking, the aqueous solution made by combining 0.006795 g $AgNO_3$ in 100 μl $H_2O$ to 25 g $H_2O$ was added directly to the first mixture, allowed to stand for 20 seconds before removal, blotting and drying.

Results
Light Stability Testing

Samples prepared by using fully aqueous soaks turned color quickly even when still wet when exposed to light. By contrast the samples prepared using the aqueous:alcohol soak were more stable to light. Telfa treated by the aqueous:alcohol bath method did not turn color at all. The texture of dressings treated with aqueous:alcohol were superior to those produced in the aqueous bath which were stiff and rigid.

Antimicrobial Serial Transfer: Test organism used was *Staph. aureus.*
Antimicrobial Serial Transfer: Test organism used was *Staph. aureus.*

| | Zone of Inhibition (mm)/Size of Sample Days of transfer | | | | |
|---|---|---|---|---|---|
| Sample | 1 | 2 | 3 | 4 | 5 |
| NuGaauze ($H_2O$) | 8.5/5 | 9/6 | 7/6 | 6/5.5 | 0 |
| NuGauze | 8/5 | 9/6 | 7/6 | 5.5/5.25 | 5/5 |
| Aquacel | 7.5/5 | 7/6 | 6/6 | 0 | 0 |
| Kalstat rope | 7/5 | 6/6 | 6/6 | 0 | 0 |
| Kalstat pad | 8/5 | 7/6 | 6/6 | 0 | 0 |
| Telfa ($H_2O$) | 6.5/6 | 7/6 | 7/6 | 5.5/5.25 | 0 |
| Telfa | 6.5/5 | 6/6 | 7/6 | 5.5/5.25 | 0 |
| Curity ($H_2O$) | 7/5 | 7/6 | 6/6 | 6/6 | 0 |
| Curity | 7/5 | 7/6 | 6/6 | 6/6 | 0 |

EXAMPLE 28

Stability of Silver Impregnated Hydrophilic Carboxymethyl Cellulose to Electron Beam Sterilization Methods This Example was done to examine the effects of electron beam irradiation on silver treated Aquacel Experimental Design Samples of Aquacel were impregnated with silver along with various amounts of copper ions by the following methods:

Samples were prepared by soaking specimens in aqueous:ethanol solutions made by adding 0.0888 g NaCl in 2 ml $H_2O$ with 500 μl Cu solution (0.0495 g Cu/10 g EtOH) to 25 g EtOH. After 10 seconds of soak the aqueous:alcohol solution made by combining 0.006795 g $AgNO_3$ in 100 μl $H_2O$ to 25 g EtOH was added directly to the first mixture, allowed to stand for 20 seconds before removal, blotting and drying.

Samples were prepared by soaking specimens in aqueous:ethanol solutions made by adding 0.0888 g NaCl in 2 ml H$_2$O with 500 μl Cu solution (0.0495 g Cu/10 g EtOH) to 25 g EtOH. After 10 seconds of soak the aqueous:alcohol solution made by combining 0.01359 g AgNO$_3$ in 100 μl H$_2$O to 25 g EtOH was added directly to the first mixture, allowed to stand for 20 seconds before removal, blotting and drying.

Samples were prepared by soaking specimens in aqueous:ethanol solutions made by adding 0.0888 g NaCl in 2 ml H$_2$O to 25 g EtOH. After 10 seconds of soak the aqueous::alcohol solution made by combining 0.006795 g AgNO$_3$ in 100 μl H$_2$O to 25 g EtOH was added directly to the first mixture, allowed to stand for 20 seconds before removal, blotting and drying.

All samples were then placed in medical grade aluminum foil pouches, heat sealed and dispatched to e-beam for irradiation. After their return they were tested for stability in light and for sustained release of antimicrobial activity.

Results

Light Stability Reaction Following E-Beam Irradiation:

| Out of package, following radiation | | Following prolonged exposure to light | |
|---|---|---|---|
| Sample | C-foil | Sample | C-foil |
| Sample A | White | Sample A | Dark |
| Sample B | White | Sample B | Dark |
| Sample C | White | Sample C | Dark |

The samples were equally stable against the effects of e-beam radiation regardless of the amount of copper present. Similarly increasing the dosage of silver did not increase the risk of discoloration by e-beam energy.

Antimicrobial Serial Transfer: Test organism used was *Staph. aureus*.

| | Zone of Inhibition (mm)/Size of sample Days of transfer | | | |
|---|---|---|---|---|
| Sample | 1 | 2 | 3 | 4 |
| Sample A | 9/4.5 | 6/4.5 | 5/4.5 | 0 |
| Sample B | 7.5/4.5 | 6/4.5 | 5/4.5 | 0 |
| Sample C | 7.5/4.5 | 5/4.5 | 5/4.5 | 0 |

The articles retain their antimicrobial activity following e-beam irradiation.

It should be understood that the foregoing relates only to preferred embodiments of the present invention and that numerous modifications or alterations may be made therein without departing from the spirit and the scope of the invention as set forth in the appended claims.

What is claimed is:

1. A method for making a wound dressing for external application to a wound, the wound dressing comprised of hydrophilic polymer fibers and containing silver chloride comprising:
    adding to the hydrophilic polymer fibers, in no particular order, a first organic solvent solution of a silver cation-donating compound, wherein the first organic solvent is a substantially nonaqueous solvent selected from alcohols, glycols, ketones, ether and ester solvents, and a second organic solvent solution of a chloride anion-donating compound, wherein the second organic solvent is a substantially nonaqueous solvent selected from alcohols, glycols, ketones, ether and ester solvents, and comprising about 5% to 15% of an aqueous solution.

2. The method of claim 1, wherein the hydrophilic polymer fibers comprise carboxymethyl cellulose.

3. The method of claim 1, wherein the hydrophilic polymer fibers comprise hydroxymethyl cellulose, cotton, rayon, alginates, calcium alginates, collagen hyaluronic acid, and dextrans.

4. The method of claim 1, wherein the silver cation-donating compound comprises silver nitrate, silver acetate, silver citrate, or silver sulphate.

5. The method of claim 1, wherein the chloride anion-donating compound comprises sodium chloride, potassium chloride, copper chloride, ferric chloride, zinc chloride, calcium chloride or hydrochloric acid.

6. The method of claim 1, wherein the anions of the second organic solvent solution are in an excess of the cations of the first organic solvent solution.

7. The method of claim 1, wherein the first organic solvent solution comprises 5% to 15% of an aqueous solution.

8. The method of claim 1, wherein the first organic solvent solution is less than 50% aqueous.

9. The method of claim 1, wherein the second organic solvent solution is less than 50% aqueous.

10. The method of claim 1, wherein the hydrophilic polymer fibers are cross-linked without using an additional cross-linking agent.

11. A method for making a wound dressing network comprised of hydrophilic polymer fibers containing silver chloride comprising:
    adding to the hydrophilic polymer fibers, in no particular order, a first organic solvent solution of a silver canon-donating compound, wherein the first organic solvent is a substantially nonaqueous solvent, and a second organic solvent solution of a chloride anion-donating compound, wherein the second organic solvent is a substantially nonaqueous solvent comprising about 5% to 15% of an aqueous solution.

12. The method of claim 11, wherein the first organic solvent solution comprises 5% to 15% of an aqueous solution.

13. The method of claim 11, wherein the first organic solvent solution is less than 50% aqueous.

14. The method of claim 11, wherein the hydrophilic polymer fibers comprise carboxymethyl cellulose.

15. The method of claim 11, wherein the hydrophilic polymer fibers comprise hydroxymethyl cellulose, cotton, rayon, alginates, calcium alginates, collagen hyaluronic acid, and dextrans.

16. The method of claim 11, wherein the silver cation-donating compound comprises silver nitrate, silver acetate, silver citrate, or silver sulphate.

17. The method of claim 11, wherein the chloride anion-donating compound comprises sodium chloride, potassium chloride, copper chloride, ferric chloride, zinc chloride, calcium chloride or hydrochloric acid.

18. The method of claim 11, wherein the anions of the second organic solvent solution are in an excess of the cations of the first organic solvent solution.

19. The method of claim 11, wherein the hydrophilic polymer fibers are cross-linked without using an additional cross-linking agent.

20. A hydrophilic antimicrobial fiber comprising,
    a hydrophilic polymer of a wound dressing for external application to a wound, wherein the hydrophilic polymer of the wound dressing contains a silver salt compound, wherein the silver salt compound is formed by reacting a chloride-containing anionic organic solution that is substantially nonaqueous and comprises about 5% to 15% of an aqueous solution, and a silver-containing cationic organic solution that is substantially nonaqueous.

21. The fiber of claim 20, wherein the silver salt compound is substantially formed on the hydrophilic polymer of the wound dressing.

22. The fiber of claim 20, wherein the silver salt compound is substantially formed within the hydrophilic polymer of the wound dressing.

23. The fiber of claim 20, wherein the silver salt compound is dispersed throughout the hydrophilic polymer of the wound dressing.

24. The fiber of claim 20, wherein the hydrophilic polymer is a cross-linked polymer.

25. The fiber of claim 20, wherein the silver salt compound is silver chloride.

26. The fiber of claim 20, wherein the hydrophilic polymer comprises carboxymethyl cellulose.

27. The fiber of claim 20, wherein the hydrophilic polymer fibers comprise hydroxymethyl cellulose, cotton, rayon, alginates, calcium alginates, collagen hyaluronic acid, and dextrans.

28. The fiber of claim 20, wherein the silver-containing cationic organic solution comprises silver nitrate, silver acetate, silver citrate, or silver sulphate.

29. The fiber of claim 20, wherein the chloride-containing anionic organic solution comprises sodium chloride, potassium chloride, copper chloride, ferric chloride, zinc chloride, calcium chloride or hydrochloric acid.

30. The fiber of claim 20, wherein the anions of the chloride-containing anionic organic solution are in an excess of the cations of the silver-containing cationic organic solution.

31. The fiber of claim 20, wherein the silver-containing cationic organic solution is less than 50% aqueous.

32. The fiber of claim 20, wherein the silver-containing cationic organic solution comprises 5% to 15% of an aqueous solution.

33. A hydrophilic antimicrobial wound dressing for external application to a wound comprising:
a hydrophilic polymer fiber network containing a concentration of a silver chloride compound, wherein the silver chloride compound is formed by reacting a chloride-containing anionic organic solution that is substantially nonaqeuous and comprises about 5% to 15% of an aqueous solution, and a silver-containing cationic organic solution that is substantially nonaqueous.

34. The wound dressing of claim 33, wherein the silver chloride compound is substantially formed on the hydrophilic polymer fiber network of the wound dressing.

35. The wound dressing of claim 33, wherein the silver chloride compound is substantially formed within the hydrophilic polymer fiber network of the wound dressing.

36. The wound dressing of claim 33, wherein the silver chloride compound is dispersed throughout the hydrophilic polymer fiber network of the wound dressing.

37. The wound dressing of claim 33, wherein the silver-containing cationic organic solution comprises 5% to 15% of an aqueous solution.

38. The wound dressing of claim 33, wherein the silver-containing cationic organic solution is less than 50% aqueous.

39. The wound dressing of claim 33, wherein the hydrophilic polymer fiber network comprises carboxymethyl cellulose.

40. The wound dressing of claim 33, wherein the hydrophilic polymer fibers comprise hydroxymethyl cellulose, cotton, rayon, alginates, calcium alginates, collagen hyaluronic acid, and dextrans.

41. The wound dressing of claim 33, wherein the silver-containing cationic organic solution comprises silver nitrate, silver acetate, silver citrate, or silver sulphate.

42. The wound dressing of claim 33, wherein the chloride-containing anionic organic solution comprises sodium chloride, potassium chloride, copper chloride, ferric chloride, zinc chloride, calcium chloride or hydrochloric acid.

43. The wound dressing of claim 33, wherein the anions of the chloride-containing anionic organic solution are in an excess of the cations of the silver-containing cationic organic solution.

44. The wound dressing of claim 33, wherein the hydrophilic polymer fiber network is cross-linked without using an additional cross-linking agent.

45. A method for applying at least one active antimicrobial agent to a wound dressing for external application to a wound comprising:
providing a biocompatible polymeric fiber, wherein the fiber comprises a hydrophilic polymer network and a silver chloride compound, wherein the silver chloride compound is formed by reacting, in no particular order, a chloride-containing anionic first organic solution comprising about 5% to 15% of an aqueous solution, and a silver-containing cationic second organic solution, wherein the first and second organic solutions are selected from alcohols, glycols, ketones, ether or ester solvents.

46. The method of claim 45, wherein the silver chloride compound is substantially formed on the fiber.

47. The method of claim 45, wherein the silver chloride compound is substantially formed within the fiber.

48. The method of claim 45, wherein the silver chloride compound is dispersed throughout the fiber.

49. The method of claim 45, wherein the fiber comprises carboxymethyl cellulose.

50. The method of claim 45, wherein the hydrophilic polymer fibers comprise hydroxymethyl cellulose, cotton, rayon, alginates, calcium alginates, collagen hyaluronic acid, and dextrans.

51. The method of claim 45, wherein the silver-containing cationic second organic solution comprises silver nitrate, silver acetate, silver citrate, or silver sulphate and the chloride-containing anionic first organic solution comprises sodium chloride, potassium chloride, copper chloride, ferric chloride, zinc chloride, calcium chloride or hydrochloric acid.

52. The method of claim 45, wherein the anions of the chloride-containing anionic first organic solution are in an excess of the cations of the silver-containing cationic second organic solution.

53. The method of claim 45, wherein the chloride-containing anionic first organic solution is substantially nonaqueous and the silver-containing cationic second organic solution is substantially nonaqueous.

54. The method of claim 45, wherein [the chloride-containing anionic first organic solution comprises 5% to 15% of an aqueous solution and] the silver-containing cationic second organic solution comprises 5% to 15% of an aqueous solution.

55. The method of claim 45, wherein [the chloride-containing anionic first organic solution is less than 50% aqueous and] the silver-containing cationic second organic solution is less than 50% aqueous.

56. A wound dressing having antimicrobial properties for external application to a body comprising:
  at least one strand of a plurality of polymeric fibers comprising:
  (a) silver as an antimicrobial agent formed by addition of, in no particular order, an organic solvent solution of a silver cation-donating compound and an organic solvent solution of a chloride anion-donating compound, wherein the organic solvent solution of the chloride anion-donating compound is a substantially nonaqueous solvent comprising about 5% to 15% of an aqueous solution; and
  (b) at least one agent that affects the rate of release of the silver from the polymeric fibers over a period of time when the polymeric fibers are hydrated,
  wherein the polymeric fibers are hydrophilic, absorbent, and hydratable; and
  wherein the silver is stabilized against color changes when exposed to light.

57. The wound dressing of claim 56, wherein the polymeric fibers comprise carboxymethyl cellulose.

58. The wound dressing of claim 56, wherein the hydrophilic polymer fibers comprise hydroxymethyl cellulose, cotton, rayon, alginates, calcium alginates, collagen hyaluronic acid, and dextrans.

59. The wound dressing of claim 56, wherein the silver is a silver chloride compound.

60. The wound dressing of claim 56, wherein the at least one agent is chloride.

61. A method of dressing an external body wound comprising,
  applying to the wound a least one strand of a plurality of polymeric fibers comprising,
  (a) silver as an antimicrobial agent formed by addition of, in no particular order, an organic solvent solution of a silver cation-donating compound, and an organic solvent solution of a chloride anion-donating compound, wherein the organic solvent solution of the chloride anion-donating compound is a substantially nonaqueous solvent comprising about 5% to 15% of an aqueous solution; and
  (b) at least one agent that affects the rate of release of the silver from the polymeric fibers over a period of time when the polymeric fibers are hydrated, wherein the polymeric fibers are hydrophilic, absorbent, and hydratable; and wherein the silver is stabilized against color changes when exposed to light.

62. The method of claim 61, wherein the polymeric fibers comprise carboxymethyl cellulose.

63. The method of claim 61, wherein the hydrophilic polymer fibers comprise hydroxymethyl cellulose, cotton, rayon, alginates, calcium alginates, collagen hyaluronic acid, and dextrans.

64. The method of claim 61, wherein the at least one agent is chloride.

65. The method of claim 61, wherein the polymeric fibers are cross-linked without using an additional cross-linking agent.

66. A method of forming a wound dressing having antimicrobial properties for external application to a body, the method comprising substantially incorporating on at least one strand of a plurality of polymeric fibers
  (a) silver as an antimicrobial agent formed by addition of, in no particular order, an organic solvent solution of a silver cation-donating compound, and an organic solvent solution of a chloride anion-donating compound, wherein the organic solvent solution of the chloride anion-donating compound is a substantially nonaqueous solvent comprising about 5% to 15% of an aqueous solution; and
  (b) at least one agent that affects the rate of release of the silver from the polymeric fibers over a period of time when the polymeric fibers are hydrated,
  wherein the polymeric fibers are hydrophilic, absorbent and hydratable; and wherein the silver is stabilized against color changes when exposed to light.

67. The method of claim 66, wherein the polymeric fibers comprise carboxymethyl cellulose.

68. The method of claim 66, wherein the hydrophilic polymer fibers comprise hydroxymethyl cellulose, cotton, rayon, alginates, calcium alginates, collagen hyaluronic acid, and dextrans.

69. The method of claim 66, wherein the at least one agent is chloride.

70. The method of claim 66, wherein the polymeric fibers are cross-linked without using an additional cross-linking agent.

71. A method of forming a wound dressing having antimicrobial properties for external application to a body, the method comprising substantially forming within at least one strand of a plurality of polymeric fibers
  (a) silver as an antimicrobial agent formed by addition of, in no particular order, an organic solvent solution of a silver cation-donating compound, and an organic solvent: solution of a chloride anion-donating compound wherein the organic solvent solution of the chloride anion-donating compound is a substantially nonaqueous solvent comprising about 5% to 15% of an aqueous solution; and
  (b) at least one agent that affects the rate of release of the silver from the polymeric fibers over a period of time when the polymeric fibers are hydrated,
  wherein the polymeric fibers are hydrophilic, absorbent and hydratable, and wherein the silver is stabilized against color changes when exposed to light.

72. The method of claim 71, wherein the polymeric fibers comprise carboxymethyl cellulose.

73. The method of claim 71, wherein the hydrophilic polymer fibers comprise hydroxymethyl cellulose, cotton, rayon, alginates, calcium alginates, collagen hyaluronic acid, and dextrans.

74. The method of claim 71, wherein the at least one agent is chloride.

75. The method of claim 71, wherein the polymeric fibers are cross-linked without using an additional cross-linking agent.

76. A method offorming a wound dressing having antimicrobial properties for external application to a body, the method comprising dispersing throughout at least one strand of a plurality of polymeric fibers
  (a) silver as an antimicrobial agent formed by addition of, in no particular order, an organic solvent solution of a silver cation-donating compound, and an organic solvent solution of a chloride anion-donating compound, wherein the organic solvent solution of the chloride anion-donating compound is a substantially nonaqueous solvent comprising about 5% to 15% of an aqueous solution; and
  (b) at least one agent that affects the rate of release of the silver from the polymeric fibers over a period of time when the polymeric fibers are hydrated,
  wherein the polymeric fibers are hydrophilic absorbent and hydratable; and wherein the silver is stabilized against color changes when exposed to light.

77. The method of claim 76, wherein the polymeric fibers comprise carboxymethyl cellulose.

78. The method of claim 76, wherein the hydrophilic polymer fibers comprise hydroxymethyl cellulose, cotton, rayon, alginates, calcium alginates, collagen hyaluronic acid, and dextrans.

79. The method of claim 76, wherein the at least one agent is chloride.

80. The method of claim 76, wherein the polymeric fibers are cross-linked without using an additional cross-linking agent.

81. A method of imparting sustained, light stable antimicrobial activity to a polymeric wound dressing for external application to a body comprising:
substantially incorporating a silver chloride compound on carboxymethyl cellulose fibers by reacting a chloride-containing anionic organic solution comprising about 5% to 15% of an aqueous solution and a silver-containing cationic organic solution such that a silver chloride compound is substantially formed on the carboxymethyl cellulose fibers.

82. The method of claim 81, wherein the silver-containing cationic organic solution comprises silver nitrate, silver acetate, silver citrate, or silver sulphate and the chloride-containing anionic organic solution comprises sodium chloride, potassium chloride, copper chloride, ferric chloride, zinc chloride, calcium chloride or hydrochloric acid.

83. The method of claim 81, wherein the anions of the chloride-containing anionic organic solution are in an excess of the cations of the silver-containing cationic organic solution.

84. The method of claim 81, wherein the chloride-containing anionic organic solution is substantially nonaqueous and the silver-containing cationic organic solution is substantially nonaqueous.

85. A method of imparting sustained, light stable antimicrobial activity to a polymeric wound dressing for external application to a body comprising:
substantially forming a silver chloride compound within carboxymethyl cellulose fibers by reacting a chloride-containing anionic organic solution comprising about 5% to 15% of an aqueous solution and a silver-containing cationic organic solution such that a silver chloride compound is substantially formed within the carboxymethyl cellulose fibers.

86. The method of claim 85, wherein the silver-containing cationic organic solution comprises silver nitrate, silver acetate, silver citrate, or silver sulphate and the chloride-containing anionic organic solution comprises sodium chloride, potassium chloride, copper chloride, ferric chloride, zinc chloride, calcium chloride or hydrochloric acid.

87. The method of claim 85, wherein the anions of the chloride-containing anionic organic solution are in an excess of the cations of the silver-containing cationic organic solution.

88. The method of claim 85, wherein the chloride-containing anionic organic solution is substantially nonaqueous and the silver-containing cationic organic solution is substantially nonaqueous.

89. A method of imparting sustained, light stable antimicrobial activity to a polymeric wound dressing for external application to a body comprising:
dispersing a silver chloride compound throughout carboxymethyl cellulose fibers by reacting a chloride-containing anionic organic solution comprising about 5% to 15% of an aqueous solution and a silver-containing cationic organic solution such that a silver chloride compound is dispersed throughout the carboxymethyl cellulose fibers.

90. The method of claim 89, wherein the silver-containing cationic organic solution comprises silver nitrate, silver acetate, silver citrate, or silver sulphate and the chloride-containing anionic organic solution comprises sodium chloride, potassium chloride, copper chloride, ferric chloride, zinc chloride, calcium chloride or hydrochloric acid.

91. The method of claim 89, wherein the anions of the chloride-containing anionic organic solution are in an excess of the cations of the silver-containing cationic organic solution.

92. The method of claim 89, wherein the chloride-containing anionic organic solution is substantially nonaqueous and the silver-containing cationic organic solution is substantially nonaqueous.

93. A method of impregnating a carboxymethyl cellulose fibrous material with a metal salt compound comprising:
substantially incorporating on a carboxymethyl cellulose fibrous material a metal salt compound by reacting a chloride-containing anionic organic solution comprising about 5% to 15% of an aqueous solution and a silver-containing cationic organic solution such that a metal salt compound is substantially formed on the carboxymethyl cellulose fibrous material.

94. The method of claim 93, wherein the chloride-containing anionic organic solution and the silver-containing catiomic organic solution are substantially nonaqueous.

95. The method of claim 93, wherein the silver-containing cationic organic solution comprises silver nitrate, silver acetate, silver citrate, or silver sulphate and the chloride-containing anionic organic solution comprises sodium chloride, potassium chloride, copper chloride, ferric chloride, zinc chloride, calcium chloride or hydrochloric acid.

96. The method of claim 93, wherein the carboxymethyl cellulose fibrous material is shaped into a film, a sheet, a fiber, or a molded article.

97. A method of impregnating a carboxymethyl cellulose fibrous material with a metal salt compound comprising:
substantially forming within a carboxymethyl cellulose fibrous material a metal salt compound by reacting a chloride-containing anionic organic solution comprising about 5% to 15% of an aqueous solution and a silver-containing cationic organic solution such that a metal salt compound is substantially formed within the carboxymethyl cellulose fibrous material.

98. The method of claim 97, wherein the chloride-containing anionic organic solution and the silver-containing cationic organic solution are substantially nonaqueous.

99. The method of claim 97, wherein the carboxymethyl cellulose fibrous material is shaped into a film, a sheet, a fiber, or a molded article.

100. A method of impregnating a carboxymethyl cellulose fibrous material with a metal salt compound comprising:
dispersing throughout a carboxymethyl cellulose fibrous material a metal salt compound by reacting a chloride-containing anionic organic solution comprising about 5% to 15% of an aqueous solution and a silver-containing cationic organic solution such that a metal salt compound is dispersed throughout the carboxymethyl cellulose fibrous material.

101. The method of claim 100, wherein the chloride-containing anionic organic solution and the silver-containing cationic organic solution are substantially nonaqueous.

102. The method of claim 100, wherein the anions of the chloride-containing anionic organic solution are in an excess of the cations of the silver-containing cationic organic solution.

103. The method of claim 100, wherein the carboxymethyl cellulose fibrous material is shaped into a film, a sheet, a fiber, or a molded article.

104. A method of making a wound dressing comprising:
adding to a hydrophilic polymer fiber matrix containing chloride ions, an organic solvent solution of a silver cation-donating compound, wherein the organic solvent is a substantially nonaqueous solvent comprising about 5% to 15% of an aqueous solution, and the chloride ions are in excess of the cations of the silver cation-donating compound in the organic solvent solution, such that a silver salt compound is dispersed throughout the hydrophilic polymer fiber.

105. The method of claim 104, wherein the hydrophilic polymer fiber matrix comprises carboxymethyl cellulose, hydroxymethyl cellulose, cotton, rayon, alginates, calcium alginates, collagen hyaluronic acid, and dextrans.

* * * * *